(12) United States Patent
Bernstein et al.

(10) Patent No.: US 11,261,250 B2
(45) Date of Patent: Mar. 1, 2022

(54) BI-SPECIFIC MOLECULE FOR CELL-SPECIFIC NOTCH INHIBITION AND RELATED METHODS AND COMPOSITIONS

(71) Applicants: Fred Hutchinson Cancer Research Center, Seattle, WA (US); The Board of Trustees of The Leland Stanford Junior University, Palo Alto, CA (US)

(72) Inventors: Irwin Bernstein, Seattle, WA (US); Vincent Luca, Palo Alto, CA (US); Kenan Christopher Garcia, Menlo Park, CA (US)

(73) Assignees: FRED HUTCHINSON CANCER RESEARCH CENTER, Seattle, WA (US); THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 228 days.

(21) Appl. No.: 16/318,313

(22) PCT Filed: Jul. 20, 2017

(86) PCT No.: PCT/US2017/043059
§ 371 (c)(1),
(2) Date: Jan. 16, 2019

(87) PCT Pub. No.: WO2018/017827
PCT Pub. Date: Jan. 25, 2018

(65) Prior Publication Data
US 2019/0248894 A1 Aug. 15, 2019

Related U.S. Application Data

(60) Provisional application No. 62/365,855, filed on Jul. 22, 2016.

(51) Int. Cl.

| | | |
|---|---|---|
| *C07K 14/705* | (2006.01) | |
| *C07K 14/475* | (2006.01) | |
| *C07K 16/28* | (2006.01) | |
| *C07K 19/00* | (2006.01) | |
| *C12N 15/63* | (2006.01) | |
| *C12N 5/10* | (2006.01) | |
| *C07K 16/22* | (2006.01) | |
| *A61P 35/00* | (2006.01) | |
| *C07K 16/46* | (2006.01) | |
| *G01N 33/566* | (2006.01) | |
| *G01N 33/574* | (2006.01) | |

(52) U.S. Cl.
CPC .......... *C07K 16/2803* (2013.01); *A61P 35/00* (2018.01); *C07K 14/475* (2013.01); *C07K 14/705* (2013.01); *C07K 16/22* (2013.01); *C07K 16/2896* (2013.01); *C07K 16/46* (2013.01); *C07K 19/00* (2013.01); *C12N 5/10* (2013.01); *C12N 15/63* (2013.01); *G01N 33/566* (2013.01); *G01N 33/574* (2013.01); *C07K 14/70596* (2013.01); *C07K 2317/31* (2013.01); *C07K 2317/622* (2013.01); *C07K 2317/70* (2013.01); *C07K 2317/76* (2013.01); *C07K 2319/00* (2013.01); *C07K 2319/74* (2013.01)

(58) Field of Classification Search
CPC ....................... C07K 2317/73; C07K 2317/92; C07K 16/22; C07K 2317/76; C07K 2317/622; C07K 2319/00; C07K 16/28; C07K 2317/31; C07K 16/2863; C07K 16/30; C07K 16/2896; C07K 14/71; C07K 2319/33; C07K 14/475; C07K 19/00; A61K 2039/505; A61K 39/3955; A61K 39/0011; A61K 39/39558; A61K 47/6849; A61K 39/395
See application file for complete search history.

(56) References Cited

U.S. PATENT DOCUMENTS

| | | | | |
|---|---|---|---|---|
| 2010/0015058 | A1 | 1/2010 | Li et al. | |
| 2013/0323266 | A1* | 12/2013 | Hoey ................. | A61K 31/7068 424/172.1 |
| 2014/0286955 | A1* | 9/2014 | Aifantis ............. | A61K 39/3955 424/139.1 |

FOREIGN PATENT DOCUMENTS

| | | |
|---|---|---|
| WO | 2013/086436 A1 | 6/2013 |
| WO | 2015/089344 A1 | 6/2015 |
| WO | 2015/187815 A1 | 12/2015 |

OTHER PUBLICATIONS

Kannan et al. Notch activation inhibits AML growth and survival: a potential therapeutic approach. J Exp Med 210(2): 321-337, 2013.*

(Continued)

*Primary Examiner* — Bridget E Bunner
(74) *Attorney, Agent, or Firm* — Christensen O'Connor Johnson Kindness PLLC

(57) ABSTRACT

This disclosure provides compositions and related methods providing targeted cell-specific inhibition of Notch receptor signaling. The disclosure provides a bi-specific molecule with separate domains that target the intended cell-type and the Notch receptor on that cell-type. The disclosure also provides for nucleic acids, vectors, and cells allowing for the expression of the bi-specific fusion molecules. The disclosure also provides related methods of making and using the bi-specific fusion molecule to inhibit Notch signaling in target cells of interest, including for the treatment of diseases characterized by a dysregulation of Notch signaling.

19 Claims, 7 Drawing Sheets
Specification includes a Sequence Listing.

(56) References Cited

OTHER PUBLICATIONS

Lobry et al. Notch pathway activation targets AML-initiating cell homeostasis and differentiation. J Exp Med 210(2): 301-319, 2013.*
Ono et al. Targeting Notch-1 positive acute leukemia cells by novel fucose-bound liposomes carrying daunorubicin. Oncotarget 7(25): 38586-38597, May 2016.*
International Search Report and Written Opinion dated Dec. 1, 2017, issued in corresponding International Application No. PCT/US2017/43059, filed Jul. 20, 2017, 16 pages.
Luca, V.C., et al., "Structural Basis for Notch1 Engagement of Delta-Like 4," Science 347(6224):847-853, Feb. 2015. (Author Manuscript provided, PMCID: PMC4445638, available in PMC May 27, 2015, 16 pages.).
McDermott, D.F., and M.B. Atkins, "PD-1 as a Potential Target in Cancer Therapy," Cancer Medicine 2(5):662-673, Oct. 2013.
Saalbach, A., et al., "Interaction of Human Thy-1 (CD 90) With the Integrin αvβ3 (CD51/CD61): An Important Mechanism Mediating Melanoma Cell Adhesion to Activated Endothelium," Oncogene 24(29):4710-4720, Jul. 2005.
Tian, D.-M., et al., "Endothelium-Targeted Delta-Like 1 Promotes Hematopoietic Stem Cell Expansion Ex Vivo and Engraftment in Hematopoietic Tissues In Vivo," Stem Cell Research 11(2):693-706, Sep. 2013.
Zhang, T., et al., "Anti-Human PD-1 Antibody BGB-A317 Exhibits Potent Immune Cell Activation," Abstract #2226, Proceedings of the AACR 107th Annual Meeting, Apr. 16-20, 2016, New Orleans, 2 pages; also Cancer Research 76(Suppl. 14):2226-2226, Jul. 2016.
Delaney, C., et al., "Notch-Mediated Expansion of Human Cord Blood Progenitor Cells Capable of Rapid Myeloid Reconstitution," Nature Medicine 16(2):232-237, Feb. 2010 (Author Manuscript, 17 pages).
D'souza, B., et al., "Canonical and non-canonical Notch ligands," Curr Top Dev Biol 92:73-129, Available online Sep. 2010 (Author Manuscript).
Espinoza, I., and L. Miele, "Notch inhibitors for cancer treatment," Pharmacology & Therapeutics 139(2):95-110, Aug. 2013 (Author Manuscript, 36 pages).
Hu, Q., et al., "F3/contactin Acts as a Functional Ligand for Notch During Oligodendrocyte Maturation," Cell 115(2):163-175, Oct. 2003.
Luca, V.C., et al., "Structural Basis for Notch1 Engagement of Delta-Like 4," Science 347(6224):847-853, Feb. 2015.
Nowell, C.S., and F. Radtke, "Notch as a Tumour Suppressor," Nature Reviews Cancer 17:145-159, Mar. 2017.
Radtke, F., et al., "Regulation of innate and adaptive immunity by Notch," Nature Review Immunology 13:427-437, Jun. 2013.
Ranganathan, P., et al., "Notch Signaling in Solid Tumors: a Little bit of Everything but not All the Time," Nature Reviews Cancer 11:338-351, May 2011.
Rizzo, P., et al., "Rational Targeting of Notch Signaling in Cancer," Oncogene 27:5124-5131, Sep. 2008.
Schmidt, M.H., et al., "Epidermal Growth Factor-Like Domain 7 (EGFL7) Modulates Notch Signalling and Affects Neural Stem Cell Renewal," Nat Cell Biol 11(7):873-880, Jul. 2009.
Sprinzak, D., et al., "Cis Interactions Between Notch and Delta Generate Mutually Exclusive Signalling States," Nature 465(7294):86-90, May 2010 (Author Manuscript, 16 pages).
Walter, R.B., et al., "Acute Myeloid Leukemia Stem Cells and CD33-Targeted Immunotherapy," Blood 119(26):6198-6208, Jun. 2012.
Yuan, X., et al., "Notch Signaling: An Emerging Therapeutic Target for Cancer Treatment," Cancer Letters 369:20-27, Dec. 2015.
International Preliminary Report on Patentability dated Jan. 31, 2019, issued in corresponding International Application No. PCT/US2017/43059, filed Jul. 20, 2017, 11 pages.

* cited by examiner

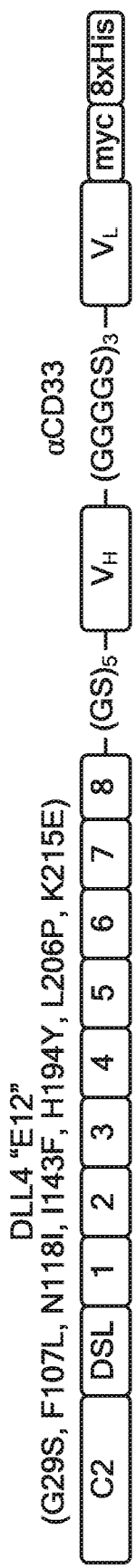
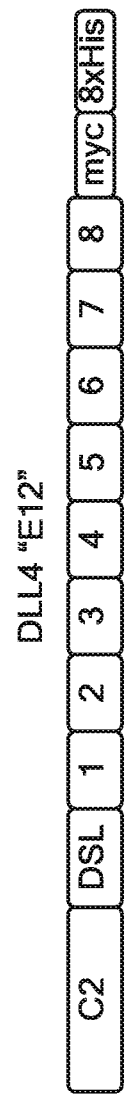
FIG. 1A
FIG. 1B
FIG. 1C

BI-SPECIFIC MOLECULE FOR CELL-SPECIFIC NOTCH INHIBITION AND RELATED METHODS AND COMPOSITIONS

CROSS-REFERENCES TO RELATED APPLICATIONS

This application is the national stage of International Patent Application No. PCT/US2017/043059, filed Jul. 20, 2017, which claims the benefit of U.S. Application No. 62/365,855, filed Jul. 22, 2016, the disclosures of both of which are hereby expressly incorporated by reference in their entirety herein.

STATEMENT OF GOVERNMENT LICENSE RIGHTS

This invention was made with government support under HL100395 awarded by the National Institutes of Health. The government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is FHTM158751_ST25.txt. The text file is 60 KB; was created on 2017-Jul.-11; and is being submitted via EFS-Web with the filing of the specification.

BACKGROUND

The Notch signaling pathway is a highly conserved pathway that facilitates cell to cell signaling in metazoan animals. Mammalian Notch receptors (Notch1, 2, 3, and 4) are Type I transmembrane receptors that are initially expressed in precursor forms with an extracellular domain (NECD), a transmembrane domain, and an intracellular domain (NICD). The precursor is cleaved by a furin convertase to provide the mature receptor with two subunits. One subunit consists of the majority of the NECD, which remains noncovalently associated with the other subunit, which contains the transmembrane domain and NICD. The NECDs of the Notch receptors have a series of epidermal growth factor (EGF)-like repeats, which play a role in ligand interaction. After the EGF repeats (toward the C-terminus of the subunit) are three cysteine-rich LIN12 and Notch (LNR) repeats, which play a role in preventing ligand-independent signaling.

Signaling is initiated when the NECD binds to an appropriate ligand presented on the surface of an opposing cell. The canonical ligands, ligands Jagged1 (e.g., GenBank Accession No. AAC51731) Jagged2 (e.g., GenBank Accession No. AAD15562), Delta-like 1 (DLL1; e.g., GenBank Accession Nos. ABC26875 or NP005609), Delta-like 3 (DLL3; GenBank Accession Nos. NP_982353.1 or NP_058637.1), or Delta-like 4 (DLL4; e.g., GenBank Accession No. NP_061947.1) (the sequence of each accession number incorporated herein by reference), are also Type I transmembrane proteins and have an extracellular domain with an N-terminal region, a cysteine-rich Delta-Serrate, and Lag2 (DSL) region, and a varying number of EGF repeats. The Notch signaling cascade is initiated by binding of a ligand to the Notch receptor on a neighboring cell. The ligand binding specifically results in a conformational change that exposes an S2 cleavage site in the NECD of the Notch receptor, permitting proteolysis. The conformational change is thought to result from a mechanical "tug" induced by the internalization by transendocytosis of the ligand into the ligand-expressing cell. Upon the initial cleavage of the Notch receptor at the S2 site, additional proteolysis occurs intracellularly to separate the NICD from the transmembrane domain. The active NICD then translocates to the nucleus and participates in a cascade of transcription activation and suppression pathways.

Regulation of Notch signaling is mediated by several mechanisms. For example, Notch receptors are subject to various post-translation modifications with the addition of sugars that can influence affinity for specific ligands or susceptibility to protease processing. Additionally, different Notch receptors have different affinities for the different ligands. Finally, cells expressing Notch receptors can also engage in cis-inhibition by co-expressing a ligand, typically distinct from the canonical ligands indicated above, that interacts with the Notch receptor without inducing proteolysis, thus preventing trans binding by a ligand expressed on a neighboring cell.

Because the general mechanism of Notch signaling operates with cell-to-cell contact, neighboring cells can mutually influence each other's gene transcription and subsequent development. These interactions permit lateral inhibition and, with the great diversity in potential regulatory mechanisms, allow groups of cells to organize and develop into complex tissues. Accordingly, Notch has been shown to play a key role in regulating cell proliferation, differentiation, development, and homeostasis. In adult mammals, Notch signaling continues to play a key role in numerous processes, including neural and hematopoietic stem cell renewal and differentiation, as well as the development of many immune cell subsets. For example, recent studies have suggested that specific interactions mediated by Notch signaling in stem cells within their specific micro-environments, also referred to as niches, contribute to the quiescence of stem cells.

The quiescent state permits self-renewal and maintenance of pluripotency of the stem cells until they are activated by distinct stimuli. This role of the micro-environment is generally illustrated by studies where quiescent stem cells that are removed from their in vivo microenvironments immediately begin to exit the quiescent state, activate, and undergo proliferation and differentiation. The specific microenvironments comprise specialized cells, in addition to other physiological characteristics, that contact the stem cells and present the appropriate ligands, including Notch-ligands, to maintain the quiescence of the stem cells.

Dysregulation of Notch signaling in different cell-types can result in a number of different inherited or acquired diseases, such as spondylocostal dysostoses, Alagille syndrome, Hajdu-Cheney syndrome, Alzheimer disease and cerebral autosomal dominant arteriopathy with subcortical infarcts, aortic valve disease, and leukoencephalopathy. Dysregulation of Notch signaling can also have oncogenic effects by further stimulating proliferation, preventing proper differentiation, and preventing apoptosis. Thus, Notch dysregulation plays a role in cancers including T-cell leukemia, breast cancer, prostate cancer, colorectal cancer, lung cancer, central nervous system (CNS) malignancies, and esophageal cancer, to name a few.

In one particular role similar in normal stem cells, Notch can be key in maintenance of pluripotency in "cancer stem cells," which serve as progenitor for various cancers. In this regard, it has been shown that many cancers appear to contain a small population of transformed pluripotent stem cells (also referred to variously as "tumor-initiating cells," "tumor propagating cells," "cancer progenitor cells," and the like), which give rise to the bulk population of cancer cells through a process of aberrant differentiation that recapitulates that of normal tissues. These cancer stem cells are characterized by properties of normal stem cells, such as indefinite self-replication through asymmetric cell division, very slow proliferation rates, and resistance to toxic agents due in part to high-level expression of ABC transporters. These cancer stem cells are able to survive for a long time in a nearly quiescent status and lead to recurrences and metastases. Thus, a complete eradication of these cells is often necessary to attain a cure for the cancer in question. As described above in the context of healthy stem cells, Notch signaling plays a central role in the quiescence of cancer stem cells, which promotes the resistant phenotype. Interrupting the quiescence of cancer stem cells can contribute to a more complete and lasting intervention.

Considering Notch's role in the survival, replication, and differentiation decisions in undifferentiated, pluripotent cancer stem cells, in addition to the role of dysregulated Notch signaling in the progression and maintenance of many diseases including cancers, Notch has been targeted for preventative and ameliorative therapies by modulating a variety of different targets affecting regulation of the Notch pathway. However, the utility of such Notch modulators have heretofore been limited due to the fact that Notch plays such a wide variety of critical roles throughout the body and that interruption of normal Notch signaling in healthy tissues leads to unacceptable toxicities and side-effects. This concept can be illustrated by the observation that elevated Notch signaling is a tumor promoter in cancers, such as described above, but normal Notch signaling has also been found to have tumor suppressor roles in other cancers, including in some keratinocytes, pancreatic and hepatocellular carcinomas, and small-cell lung cancers. Thus, systemic or non-specific targeting of Notch signaling for one purpose can have deleterious effects throughout other cells and tissues in the body, reducing the utility of such treatments.

Accordingly, notwithstanding the advances in influencing Notch signaling, there remains a need for compositions and methods to selectively target cells for Notch modulation leaving Notch signaling in non-targeted cells substantially unaffected. The present disclosure addresses this and related needs.

SUMMARY

This summary is provided to introduce a selection of concepts in a simplified form that are further described below in the Detailed Description. This summary is not intended to identify key features of the claimed subject matter, not is it intended to be used as an aid in determining the scope of the claimed subject matter.

In one aspect, the disclosure provides a bi-specific molecule for targeted inhibition of Notch signaling in a cell-type of interest. The bi-specific molecule comprises a cell-targeting domain and a Notch-binding domain. The cell-targeting domain specifically binds to an antigen characteristic of the cell-type of interest. In some embodiments, the bi-specific molecule is soluble. As incorporated into the disclosed bi-specific molecule, the Notch-binding domain does not initiate proteolysis of the Notch receptor upon binding. In some embodiments, the bi-specific molecule is antagonistic, or inhibitory, to Notch signaling in the target cell.

In another aspect, the disclosure provides related pharmaceutical compositions comprising the bi-specific molecule (or pharmaceutically acceptable salts thereof), which can optionally include pharmaceutically acceptable carriers, and the like, to facilitate appropriate administration.

In another aspect, the disclosure provides a nucleic acid that encodes a fusion protein embodiment of the bi-specific molecule, or components thereof. The disclosure also provides related vectors and cultured cells useful to facilitate the expression of the bi-specific fusion protein molecule or components thereof.

In another aspect, the disclosure provides methods of using the disclosed bi-specific molecule, including methods for modulating (e.g., inhibiting) Notch signaling in a cell-type of interest, methods for inhibiting the development of a cancer cell or cancer progenitor cell, methods for inhibiting cancer in a subject in need thereof, and methods for treating a disease treatable by inhibiting Notch signaling in a cell-type of interest. The disclosed methods comprise contacting the cell-type of interest (directly and/or via administration to a subject comprising the cell-type of interest) with an effective amount of the disclosed bi-specific molecule.

In another aspect, the disclosure provides methods of making the bi-specific molecule, including methods of screening for appropriate cell targeting domains to successfully implement the targeted inhibition functionality of the disclosed bi-specific molecule.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 1A-1C are schematic illustrations of the design for an embodiment of the disclosed bi-specific molecule incorporating a modified DLL4 with elevated affinity fused to an anti-CD33 single-chain variable fragment. FIG. 1A illustrates the overall structure of the bi-specific $DLL4_{E12}$-αCD33 scFv molecule. FIG. 1B specifically illustrates the control $DLL4_{E12}$ domain expressed without the cell-targeting domain, whereas FIG. 1C illustrates the control αCD33 scFv domain expressed without the Notch-binding domain.

FIG. 4A illustrates the relative Hes1 expression level in CD33+HL60 cells incubated with immobilized agonist in the presence of the soluble bi-specific $DLL4_{E12}$-αCD33 scFv fusion molecule, soluble agonist, or soluble control IgG molecule. FIG. 4B illustrates the relative Hes1 expression level in CD33− REH cells incubated with immobilized agonist in the presence of the soluble bi-specific $DLL4_{E12}$-αCD33 scFv fusion molecule, soluble agonist, or soluble control IgG molecule.

DETAILED DESCRIPTION

Figure 2B:
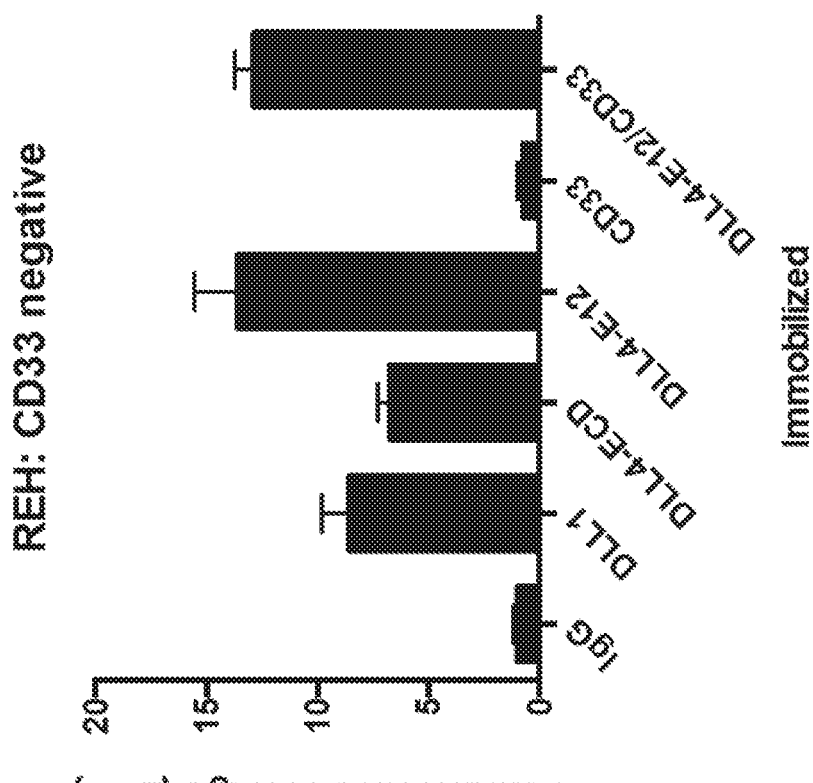
FIGS. 2A and 2B graphically illustrate the comparative activation of Notch signaling in CD33+ (FIG. 2A) and CD33− (FIG. 2B) cells upon exposure to the illustrative bi-specific $DLL4_{E12}$-αCD33 scFv molecule.

As described above, there has been extensive development of therapeutic approaches to alter Notch signaling for treating cancer and other diseases. However, considering the numerous and variable roles of Notch signaling in different tissues and cells throughout the body, interventions that alter Notch signaling in multiple tissues can lead to toxicities and other adverse side-effects that limit their usage.

Thus, as described in more detail herein, the inventors investigated soluble Notch modulators that could be specifically targeted to particular cell-types of interest. Notch ligands (typically expressed on a cell or solid support surface) are known to activate the Notch receptor by providing sufficient mechanical distortion of the Notch ECD (NECD) to permit cleavage, which ultimately leads to the release of the active NECD within the cell. The inventors have demonstrated that soluble Notch ligands, even with enhanced binding affinity achieved through specific mutations, unexpectedly inhibit rather than activate Notch receptors. The inventors further investigated whether a bi-specific molecule that simultaneously targets a Notch-binding ligand to a specific cell-type through unique antigens co-expressed on the target cell with Notch receptor can modify Notch signaling in a cell-specific manner, while avoiding substantially affecting Notch signaling on non-target cells. It was surprisingly found that a bi-specific molecule targeting CD33 on leukemic cells inhibited Notch signaling on the cells, but not CD33-cells, via a domain comprising an enhanced-affinity Notch ligand, Delta-like ligand 4 (DLL4). This result was unexpected at least because the bi-specific molecule also binds to the cell-surface CD33 antigen, and could potentially provide the mechanical alteration in Notch conformation required to activate signaling.

In accordance with the foregoing, in one aspect, the disclosure provides a bi-specific molecule for targeted inhibition of Notch signaling in a cell type of interest. The bi-specific molecule comprises a cell targeting domain that specifically binds to an antigen characteristic of the cell type of interest and a Notch binding domain.

Notch and Notch Targeting Domain

As used herein, the term "Notch signaling" or other references to the function of Notch receptor refer to the cell-signaling cascade that occurs from the proteolytic cleavage of the expressed mature Notch receptors in a cell membrane. Notch receptors in mammals include Notch1, Notch2, Notch3, and Notch4, and homologs of which are known and readily ascertainable by persons of ordinary skill in the art for humans, rodents, and other species. For example, representative amino acid sequence for human Notch1 is provided in Genbank Accession No. P46531, which is incorporated herein by reference in its entirety. This is also set forth herein as SEQ ID NO:8. Other Notch receptors are well-known and readily identifiable. Illustrative, non-limiting examples of other Notch receptors include the following sequences: GenBank Accession No. AAH71562.2 (representative human Notch2), GenBank Accession No. AAB91371.1 (representative human Notch3), and GenBank Accession No. AAC63097.1 (representative human Notch4) (the sequence of each accession number is incorporated herein by reference). Similarly, Notch is also known and readily ascertainable in *Drosophila, C. elegans*, and other invertebrate species. Signaling of Notch receptor can be ascertained and monitored with any appropriate technique familiar in the art. For example, as described in more detail below, Notch signaling can be monitored by measuring downstream gene products resulting from Notch activation, such as Hes1 expression. Alternatively, reporter systems are available to indicate Notch signaling, such as the CHO-K1 Notch reporter system. See, e.g., Sprinzak, D., et al. "Cis-interactions between Notch and Delta generate mutually exclusive signalling states," *Nature* 465(7294):86-90 (2010), incorporated herein by reference in its entirety.

As used herein, the term "targeted inhibition" refers to the relative reduction or prevention of Notch signaling in a cell or cell-type of interest compared to the Notch signaling in that cell or cell-type of interest in a comparative scenario without application of the disclosed bi-specific molecule. The term "targeted" indicates that this reduction or prevention effect is realized primarily in the cell or cell-type of interest and does not substantially occur in other cells or cell-types. While the effect is ideally realized exclusively in the cell or cell-type of interest, it will be understood that some effect can still occur in off-target cells or cell-types while remaining within the scope of the disclosure. Any reduction in off-target effect compared to non-targeted therapies still confers a utility of reducing toxicity and side-effects and, thus, is a desired result achieved by the present disclosure. In some embodiments, the disclosed bi-specific molecule does not substantially inhibit Notch signaling in on off-target cells or cell-types, e.g., cells that lack or have reduced expression of the antigen characteristic of the cell-type of interest.

The Notch binding domain of the bi-specific molecule can comprise a Notch binding domain of any Notch receptor ligand. Similarly, the Notch binding domain of the bi-specific molecule can be derived from a Notch binding domain of any Notch receptor ligand as long as the derivative retains Notch binding affinity sufficient to measurably inhibit Notch proteolysis and subsequent signaling. As used herein, the term "derived" indicates that the derivative is obtained from the source molecule or sequence, but can contain changes (e.g., substitution, deletions, additions) from the source molecule or sequence. Typically, the derivative includes substantially the same amino acid sequence as the source molecule. The derivative can also contain chemical modifications, such as to one or more amino acid residues, within the original source sequence. "Substantially the same" in certain contexts is described in terms of % sequence identity, e.g., a variant that is at least 80% identical to a parental sequence and having one or more substitutions, as determined using standard and accepted methodologies in the art. In some embodiments, the derivative can have an amino acid sequence that is at least 80%, 81%, 82%, 83%, 84%, 85%, 86%, 87%, 88%, 89%, 90%, 91%, 92%, 93%, 94%, 95%, 96%, 97%, 98%, and 99% identical to a parental sequence.

The indicated Notch receptor ligand includes any canonical or noncanonical ligand to mammalian Notch receptor (e.g., a ligand to Notch1, Notch2, Notch3, or Notch4 receptor). Such ligands can be, or can be derived from, mammalian Notch receptor ligands. As indicated above, the canonical Notch ligands in mammals include Jagged proteins (e.g., Jagged1 and Jagged2) and Delta proteins (e.g., DLL1, DLL3, DLL4; where DLL is an acronym for Delta Like Ligand), each of which are well-known and are contemplated and encompassed by this disclosure. As non-limiting examples, representative canonical Notch ligand sequences comprise sequences set forth in GenBank Accession No. AAC51731 (Jagged1), GenBank Accession No. AAD15562 (Jagged2), GenBank Accession Nos. ABC26875 or NP005609 (DLL1), GenBank Accession Nos. NP_982353.1 or NP_058637.1 (DLL3), and NP_061947.1 (DLL4) (the sequence of each accession number incorporated herein by reference), homologs, or functional (Notch binding) variants, fragments, or derivatives thereof. These canonical ligands, collectively referred to as DSL ligands, typically contain an N-terminal region, a DSL domain, and at least a first two EGF-like repeats, which are necessary for interaction with EGF repeats 11 and 12 of Notch receptors. Accordingly, in some embodiments, the Notch binding domain comprises an extracellular domain of a Delta protein or a Jagged protein, such as vertebrate (e.g., mammalian) or invertebrate Delta or Jagged proteins, as described herein. A 2.3 angstrom resolution crystal structure of interacting regions of Notch1-DLL4 indicates the structural components of the ligand-receptor complex important for binding. See Luca, V. C., et al., "Structural Basis for Notch1 Engagement of Delta-Like 4," *Science* 347(6224):847-853 (2015). Luca, et al., (2015), which is incorporated herein in its entirety, further discloses modifications in the wild-type DLL4 that enhance binding affinity to the receptor, thus further illuminating required and critical domains in a canonical Notch ligand required for binding to the Notch receptor. Accordingly, a person of ordinary skill in the art can readily identify minimal Notch binding domains from known or putative Notch ligands.

In some embodiments, the Notch binding domain can include polypeptide sequences with one or more mutations in a wild-type sequence resulting in modified affinity for the Notch receptor. For example, as demonstrated in the E12 variant of rat DLL4 disclosed in Luca, et al. (2015), mutations of G28S, F107L, L206P, N118I, I143F, H194Y, K215E, individually or in any combination, can enhance affinity of binding. Accordingly, in an illustrative, non-limiting embodiment, the Notch binding domain can comprise an amino acid sequence with at least 80% (such as about 80%, 81%, 82%, 83%, 84%, 85%, 86%, 87%, 88%, 89%, 90%, 91%, 92%, 93%, 94%, 95%, 96%, 97%, 98%, and 99%) sequence identity to the sequence set forth in SEQ ID NO:2. SEQ ID NO:2 is a wild-type polypeptide sequence of a rat DLL4 fragment corresponding to the MNNL to EGF2 domains (i.e., amino acid positions 27 to 283) of the full-length precursor. The full length rat DLL4 precursor is set forth herein as SEQ ID NO: 1. In some embodiments, the Notch binding domain comprises a polypeptide with a sequence that includes at least one substitution at an amino acid position selected from: 28, 43, 52, 96, 107, 118, 143, 146, 183, 194, 206, 215, 223, and 257 (the positions are numbered with respect to positions within the reference sequence set forth in SEQ ID NO:1 and corresponding homologous positions in other DLL proteins can be readily ascertained by alignment). In certain embodiments, the at least one substitution enhances affinity. In some embodiments, the at least one substitution is selected from: G28S, M/V43I, P52S, S96I, F107L, N118I, I143F/T, Q146K, S183N, H194Y, L206P, K215E, L223R, and N257K, or a similar substitution at a corresponding amino acid residue in a homologous sequence. In some instances, the high affinity Notch receptor ligand comprises at least 2, 3, 4, 5, 6, 7, 8, 9, 10 or more of the substitutions set forth above. Any combination of substitutions as set forth above is contemplated. Examples of specific combinations of substitutions include, but are not limited to: (i) P52S, F107L, L206P; (ii) F107L, L206P, N257K; (iii) F107L, L223R, N257K; (iv) G28S, M43I, F107L, N118I; (v) G28S, F107L, N118I, Q146K, H194Y, L206P, K215E; (vi) G28S, F107L, N118I, I143F, H194Y, L206P, K215E; (vii) G28S, M43I, S96I, N118I, I143T, S183N, H194Y, L206P, K215E; (viii) G28S, F107L, L206P; and (ix) G28S, F107L, L206P, N257K (or a similar substitution at a corresponding amino acid residue in a homologous sequence).

Also disclosed in Luca, et al. (2015), mutations to Jagged proteins could be mapped to the sequence of DLL4 indicating important residues on this ligand for contact and binding on the Notch receptor. Thus, the Notch binding domain can comprise an amino acid sequence with at least 80% (such as about 80%, 81%, 82%, 83%, 84%, 85%, 86%, 87%, 88%, 89%, 90%, 91%, 92%, 93%, 94%, 95%, 96%, 97%, 98%, and 99%) sequence identity to the sequence set forth in SEQ ID NO:5, which sets forth the amino acid sequence corresponding to the amino acids 32 to 295 of the full wild type rat Jagged1 polypeptide. The full wild type rat Jagged1 polypeptide sequence is set forth in SEQ ID NO:4. In additional embodiments, the Notch binding domain can comprise at least one substitution at an amino acid position selected from 100 and 182, with reference to positions in SEQ ID NO:4 (although not requiring the entire sequence; homologous positions in other DLL proteins can be readily ascertained by alignment). In certain embodiments, the at least one substitution is selected from: P100H, Q183P, and a combination thereof. Alternatively, in homologous sequences, the at least on substitution can be at the corresponding amino acid residue position(s) in the homologous sequence.

In other embodiments, the Notch binding domain can comprise an amino acid sequence with at least 80% (such as about 80%, 85%, 90%, 91%, 92%, 93%, 94%, 95%, 96%, 97%, 98%, 99%, or 100%) sequence identity to the sequence set forth in SEQ ID NO:6 or 7, which set forth the amino acid sequence of the extracellular Notch-binding regions of representative human Jagged2 (Genbank Accession No. AAD15562.1) and human Delta like 1 (DLL1; Genbank Accession No. NP005609.3), respectively. In view of the above structural studies and other available data, persons of ordinary skill in the art can readily ascertain permissible variations in the reference sequences that still result in functional binding to the Notch receptors.

In addition to Notch binding domains of canonical Notch ligands, the Notch binding domain of the bi-specific molecule can comprise a Notch binding domain (or a Notch-binding derivative or fragment thereof) of any non-canonical Notch receptor ligand, such as the binding domain of Dlk1, Dlk2, DNER, EGFL 7, and F3/contactin, which are more typically involved in cis-inhibition. See, e.g., Hu, Q., et al., "F3/contactin acts as a functional ligand for Notch during oligodendrocyte maturation," *Cell* 115(2):163-175 (2003); Schmidt, M. H., et al., "Epidermal growth factor-like domain 7 (EGFL7) modulates Notch signalling and affects neural stem cell renewal," *Nat Cell Biol* 11(7):873-880 (2009); and D'Souza, B., et al., "Canonical and non-canonical Notch ligands," *Curr Top Dev Biol* 92:73-129 (2010), each of which is incorporated herein by reference in its entirety. The fragments or derivatives retain the ability to bind the target Notch receptor. In some embodiments, the derivative can comprise an amino acid sequence with at least 80% (such as about 80%, 81%, 82%, 83%, 84%, 85%, 86%, 87%, 88%, 89%, 90%, 91%, 92%, 93%, 94%, 95%, 96%, 97%, 98%, and 99%) of the sequence of the source Notch binding domain of the non-canonical Notch receptor ligand.

While the above description included examples of rat or human Notch ligands, it will be appreciated that the indicated mammalian sources for Notch ligands can include the non-limiting examples of primates (including, e.g., human, monkey, and the like), rodent (including, e.g., rat, mouse, guinea pig, and the like), dog, cat, horse, cow, pig, sheep, and the like. Non-mammalian Notch ligands, such as *Drosophila* Serrate and Delta, are also well-known and are encompassed by the present disclosure. As indicated, the Notch signaling system is highly conserved and, thus, homologous sequence positions among the Notch receptors and respective Notch ligands are readily ascertainable by persons of ordinary skill in the art.

In addition to Notch binding domain comprising or being derived from a known Notch receptor ligand, as described above, the Notch binding domain of the disclosed bi-specific molecule can also be or comprise an affinity reagent designed to specifically bind a Notch receptor. As used herein, "affinity reagent" refers to any molecule that can bind a target antigen, in this case a Notch receptor, with a specific affinity (i.e., detectable over background). Exemplary, non-limiting categories of affinity reagent include antibodies, an antibody-like molecule (including antibody derivatives and antigen (i.e., Notch)-binding fragments thereof), peptides that specifically interact with a particular antigen (e.g., peptibodies), antigen-binding scaffolds (e.g., DARPins, HEAT repeat proteins, ARM repeat proteins, tetratricopeptide repeat proteins, and other scaffolds based on naturally occurring repeat proteins, etc., [see, e.g., Boersma and Pluckthun, *Curr. Opin. Biotechnol.* 22:849-857, 2011, and references cited therein, each incorporated herein by reference in its entirety]), aptamers, or a functional Notch-binding domain or fragment thereof. These affinity reagents are described in more detail below in the "Additional definitions" section. Such affinity reagents can be generated through application of routine techniques based on the known Notch targets described above.

As used herein, the term "specifically bind" or variations thereof refer to the ability of the affinity reagent component to bind to the antigen of interest (e.g., Notch receptor or, as described below, the antigen characteristic of the cell-type of interest), without significant binding to other molecules, under standard conditions known in the art. The antigen-binding molecule can bind to other peptides, polypeptides, or proteins, but with lower affinity as determined by, e.g., immunoassays, BIAcore, or other assays known in the art. However, affinity reagent preferably does not substantially cross-react with other antigens.

In some embodiments, the Notch-binding domain of the bi-specific molecule, whether derived from a Notch-binding domain of Notch receptor ligand (e.g., DLL4) or from an affinity reagent described above (e.g., an antibody or antibody-like molecule), has a binding affinity sufficient for binding the Notch receptor of the target when sufficiently targeted by a high affinity cell-targeting domain, but does not exceed a threshold wherein the bi-specific molecule substantially binds to Notch receptors on cells that do not contain the antigen corresponding to the cell-targeting domain. Stated otherwise, the Notch binding domain of the bi-specific molecule has a limit on binding affinity for the Notch receptor such that its administration to a subject or a heterogeneous population of cells does not result in indiscriminate binding to and inhibition of Notch, regardless of cell-type. Thus, in some embodiments, the Notch-binding domain of the bi-specific molecule has a binding affinity within a range characterized by a dissociation constant ($K_d$) from about 100 nM (lower binding affinity) to about 0.1 nM (higher binding affinity). For example, the Notch-binding domain has a binding affinity for the Notch receptor characterized by ($K_d$) of about 100 nM 90 nM, 80 nM, 70 nM, 60 nM, 50 nM, 40 nM, 30 nM, 20 nM, 100 nM, 5 nM, 1 nM, and 0.1 nM. Exemplary ($K_d$) ranges include from about 100 nM to about 40 nM, from about 80 nM to about 20 nM. Other exemplary ($K_d$) ranges include from about 60 nM to about 1 nM, from about 80 nM to about 60 nM, from about 70 nM to about 50 nM, from about 60 nM to about 40 nM, from about 50 nM to about 30 nM, from about 40 nM to about 20 nM, from about 30 nM to about 100 nM, from about 20 nM to about 1 nM, from about 100 nM to about 0.01 nM, and any subrange therein. As indicated above, while sufficient binding affinity between the Notch-binding domain of the bi-specific molecule and the Notch receptor is required to functionally inhibit activation by other ligands, the affinity should not be so high as to induce indiscriminate binding of the bi-specific molecule throughout the body of a subject if given a systemic administration of the bi-specific molecule. Such systemic Notch binding would counteract the intended cell-specific functionality of the disclosed bi-specific molecule. Instead, cell-specificity is conferred by the cell-targeting domain, which has a higher affinity for an antigen characteristic of the target cell of interest, which is now described.

Cell Targeting Domain

As indicated above, the cell-targeting domain specifically binds to an antigen characteristic of the cell-type of interest. The cell-targeting domain typically binds to the antigen characteristic of the cell-type of interest with an affinity that is at least greater than the binding affinity of the Notch-binding domain for the Notch receptor, as described above. In some cases, cell-targeting domain typically binds to the antigen characteristic of the cell-type of interest with an affinity that is at least about 2 times, 3 times, 4 times, 5 times, 6 times, or 7 times greater than the binding affinity of the Notch-binding domain for the Notch receptor. In some instances, the binding affinity of the cell-targeting domain for the antigen characteristic of the cell-type of interest is at least an order of magnitude greater than the binding affinity of the Notch binding domain for a Notch receptor. For example, the dissociation constant ($K_d$) characterizing the affinity of the cell-targeting domain for the antigen characteristic of the cell-type of interest can be about 50 nM, 40 nM, 30 nM, 20 nM, 10 nM, 5 nM, 1 nM, 0.75 nM, 0.5 nM, 0.1 nM, 0.05 nM, 0.01 nM, 0.005 nM, and 0.001 nM, or even smaller. Typical ($K_d$) ranges characterizing the binding affinity of the cell-targeting domain for the antigen characteristic of the cell-type of interest include from about 30 nM to about 10 nM, from about 20 nM to about 1 nM, from about 10 nM to about 0.1 nM, from about 0.5 nM to about 0.05 nM, and from about 0.1 nM to about 0.001 nM, or even lower, or any subrange therein.

The cell-targeting domain comprises an affinity reagent designed to specifically bind to an antigen characteristic of the cell-type of interest. In this context, the term "affinity reagent" refers to any molecule that can bind the antigen characteristic of the cell-type of interest with a specific affinity (i.e., detectable over background). As with the above description with respect to the Notch-binding domain, exemplary, non-limiting categories of affinity reagent include antibodies, an antibody-like molecule (including antibody derivatives and antigen (i.e., cell-specific antigen)-binding fragments thereof), peptides that specifically interact with a particular antigen (e.g., peptibodies), antigen-binding scaffolds (e.g., DARPins, HEAT repeat proteins, ARM repeat proteins, tetratricopeptide repeat proteins, and other scaffolds based on naturally occurring repeat proteins, etc., [see, e.g., Boersma and Pluckthun, *Curr. Opin. Biotechnol.* 22:849-857, 2011, and references cited therein, each incorporated herein by reference in its entirety]), aptamers, or a functional Notch-binding domain or fragment thereof. Again, these affinity reagents are described in more detail below in the "Additional definitions" section.

The antigen characteristic of a cell-type of interest can be any relevant antigen known to be predominantly present and accessible on a target cell. The chosen antigen is preferably substantially absent or reduced (e.g., expressed at lower levels) in non-target cells so as to confer specific and preferential binding on the bi-specific molecule for the target cell. Thus, the term antigen "characteristic" of a cell-type of interest is not intended to indicate that the antigen is exclusive to the target cell-type but rather the expression or elevated level of expression is at least typical of the target cell-type and distinguishes that cell-type from the majority of other cells. As indicated above, any targeting that reduces indiscriminate binding of the molecule to Notch receptors systemically throughout the body is advantageous for therapeutic interventions. In some cases, the binding affinity of the Notch binding domain is such that binding to a Notch receptor will first require the cell-targeting domain to bind to a co-expressed antigen.

Persons of ordinary skill in the art can readily select any appropriate antigen for the design and implementation of the cell-targeting domain according to the vast cataloguing of characteristic target cell biomarkers known in the art.

In some embodiments, the antigen is a cell surface biomarker for a cancer cell or a cancer progenitor cell. As used herein, the term "cancer" refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. The term "cancer progenitor cell" is interchangeable with terms such as "cancer stem cell," "tumor propagating cells," and "tumor-initiating cells," all of which refer to pluripotent cells that themselves may be benign but give rise to cancer cells through a process of aberrant differentiation. These progenitor cells exhibit indefinite self-replication through asymmetric cell division, often have very slow proliferation rates, and are often resistant to toxic agents due in part to high-level expression. Many types of cancers are known to those of skill in the art, including solid tumors such as carcinomas, sarcomas, glioblastomas, melanomas, lymphomas, myelomas, etc., and circulating cancers such as leukemias. Cancers of virtually every tissue are known, and functional roles of Notch have been established in many cancers, such as influencing tumor initiation, tumor progression, tumor maintenance, drug resistance, and the like. For example, relevant discussions of Notch signaling as a target in cancer intervention are provided in Rizzo, P., et al., "Rational targeting of Notch signaling in cancer," *Oncogene* 27:5124-5131 (2008); Ranganathan, P., et al., "Notch signaling in solid tumors: a little bit of everything but not all the time," *Nature Reviews Cancer* 11:338-351 (2011); Espinoza, I. and L. Miele, "Notch inhibitors for cancer treatment," *Pharmacology & Therapeutics* 139:95-110 (2013); and Yuan, X., et al., "Notch signaling: An emerging therapeutic target for cancer treatment," *Cancer Letters* 369:20-27 (2015), each of which is incorporated herein by reference in its entirety. Illustrative cancers or cancer cell types encompassed by the present disclosure include but are not limited to ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer. In some embodiments, the cancer cell is selected from T (leukemic) cell, breast cancer cell, prostate cell, lung cancer cell, glioblastoma, colo-rectal cancer cell, cervical cancer cell, melanoma cancer cell, pancreatic cancer cell, esophageal cancer cell, and the like, or a progenitor of any of the foregoing.

Cancer antigens can be, for example, tumor specific or tumor associated antigens that are known in the art. Exemplary antigens that are characteristic of various cancers and their qualifications as determinants of cancer cells are discussed widely in the literature. For example, see Cheever, Martin A., et al., "The prioritization of cancer antigens: a national cancer institute pilot project for the acceleration of translational research," *Clinical Cancer Research* 15(17): 5323-5337 (2009), incorporated herein by reference in its entirety. The role of Notch signaling, and thus its potential as a therapeutic target, in a wide variety of cancer cell-types is reviewed by Rizzo, P., et al., "Rational targeting of Notch signaling in cancer," *Oncogene* 27:5124-5131 (2008) and Nowell and Radtke, "Notch as a tumour suppressor," *Nature Reviews Cancer* 17:145-159 (2017), each incorporated herein by reference in its entirety. In some embodiments, the antigen characteristic of a cell-type of interest can be a cell surface marker of any cancer or tumor type of interest. In a few illustrative, non-limiting embodiments the antigen characteristic of a cell-type of interest is CD33, CD326, or CD133.

Relevant antigens that are characteristic of the cancer cells of interest are known and domains that specifically bind to such antigens are available or can be readily produced for incorporation into the disclosed bi-specific molecule. An illustrative, non-limiting example of an antigen characteristic of a target cell-type is the cell-surface marker CD33, which is an antigen that is characteristic of some leukemic cells. As described in Walter, R. B., et al., "Acute myeloid leukemia stem cells and CD33-targeted immunotherapy," *Blood* 119(26)6198-6208 (2012), incorporated herein by reference in its entirety, the cell-surface marker CD33 is characteristic of a group of myeloid precursor cells and is an attractive antigen used in targeted immunotherapy for acute myeloid leukemias (AMLs). As described, some AMLs involve the development of a diverse population of cell lineages from the progenitor leukemic stem cells (LSCs). The several lineages of leukemic cells from such AMLs are predominantly or exclusively characterized by expression of CD33 on the cell surface at sufficient levels that it can be used as to target specific immunotherapeutic therapies for these AMLs. Accordingly, as described in more detail below, this antigen was targeted using a bi-specific molecule, referred to as DLL4$_{E12}$-αCD33 scFv fusion molecule, where the αCD33 scFv served as the cell-targeting domain to specifically target to these AML cells known to express CD33. Thus, one illustrative cell-targeting domain can have the amino acid sequence set forth in SEQ ID NO:9, or a functional variant thereof that binds to CD33. Such a functional variant of the CD33 binding domain can comprise a sequence with at least 80% (such as about 80%, 85%, 90%, 91%, 92%, 93%, 94%, 95%, 96%, 97%, 98%, 99%, or 100%) sequence identity to the sequence set forth in SEQ ID NO:9.

Linker, Fusion Constructs

In one embodiment, cell-targeting domain and the Notch-binding domain are disposed in consecutively, in any order or orientation, within the bi-specific molecule. In an alternative embodiment, the cell-targeting domain and the Notch-binding domain, in any order or orientation, are joined by at least an intervening flexible linker domain. The linker domain functions as a spacer to allow each domain sufficient space to assume its natural three-dimensional shape without requiring significant adjustment, thus allowing freedom to contact and bind their corresponding targets without mutual interference. The linker can be of sufficient length and flexibility to allow independent movement of each domain, thus maximizing their potential to locate and bind their respective targets. The linker can be a synthetic polypeptide sequence, which is typically between about four and about 40 amino acids in length (e.g., about 5, 10, 15, 20, 25, 30, 35, 40 amino acids), although it can be longer, and can be part of an expressed fusion construct. The linker is typically designed to avoid significant formation of rigid secondary structures that could reduce the flexibility or distance provided between the proximate components. Thus, the linker is designed to provide a linear or alpha-helical structure. Such linkers are commonly used and are well-understood in the art. An illustrative example of a linker is a 15 amino acid residue linker with 3× repeats of the sequence Gly-Gly-Gly-Gly-Ser, which was utilized in a specific embodiment described in more detail below.

In some embodiments, the bi-specific molecule is a fusion polypeptide and each of the cell-targeting domain and Notch binding domain are polypeptides that do not naturally occur together. The term "fusion" in the context of a fusion protein indicates that the overall protein or polypeptide contains a nonnaturally occurring polypeptide sequence. The fusion protein combines to two or more existing polypeptides or polypeptide fragments (i.e., the distinct cell-targeting and Notch-binding domains, and optionally an intervening linker), from the same or different source proteins, in a chimeric polymer where the polypeptides (or fragments) do not naturally occur together in that manner. Methods of producing fusion proteins are well known. For example, nucleic acids encoding the different polypeptide components of the fusion protein can be generated and amplified using PCR, and assembled into an expression vector in the same reading frame (with or without intervening sequence encoding a linker) to produce a fusion gene. The expression vector can be transformed into any appropriate expression system, such as prokaryotic or eukaryotic cells, which can then express the protein. See, e.g., such standard references as Coligan, Dunn, Ploegh, Speicher and Wingfield, "Current Protocols in Protein Science" (1999), Volume I and II (John Wiley & Sons Inc.); Sambrook et al., "Molecular Cloning: A Laboratory Manual" (1989), 2nd Edition (Cold Spring Harbor Laboratory Press); and Prescott, Harley and Klein. "Microbiology" (1999), 4th Edition (WBC McGraw Hill), each incorporated herein by reference in its entirety. One exemplary approach for creating fusion proteins is described in more detail in the below examples. In another embodiment, the fusion protein can be created by linking the two polypeptide fragments corresponding to the separate cell-targeting and Notch-binding domains. Each of these separate components can be generated or obtained independently from one another by any known and conventional technique. The components can subsequently be fused or linked to one another by chemical means. For example, each component can have complementary binding partner components such that they will form strong mutual bonds, thereby linking their respective components to produce the fusion protein. The linker moieties can be homobifunctional or heterobifunctional. An illustrative, nonlimiting example of such chemical binding partner components include having one component (e.g., the cell-targeting domain) include biotin and the other component (e.g., Notch binding domain) include (strept)avidin, or vice versa. The biotin and (strept) avidin moieties will form high-affinity bonds, thereby linking, or "fusing," the components to result in the fusion protein. Other common linking chemistries can also be used, such as, for example, gluteraldehyde, and the like.

In some embodiments, the bi-specific molecule is isolated. In this context, the term "isolated" indicates that the bi-specific molecule, e.g., in the form of a fusion protein, has been produced through human intervention and has been substantially separated from the materials co-existing in the production environment, such as the intracellular organelles and proteins in a cell expression system. In contrast, a naturally expressed protein in cell is not "isolated."

As described in more detail below, a bi-specific molecule, referred to as DLL4$_{E12}$-αCD33 scFv fusion molecule, with a sequence set forth in SEQ ID NO: 10, was generated and successfully applied to specifically inhibit Notch signaling on CD33+ cells. Accordingly, in some embodiments, the bi-specific molecule comprises a sequence with at least 80% (such as about 80%, 81%, 82%, 83%, 84%, 85%, 86%, 87%, 88%, 89%, 90%, 91%, 92%, 93%, 94%, 95%, 96%, 97%, 98%, 99%, or 100%) sequence identity to the sequence set forth in SEQ ID NO:10. In one embodiment, the bi-specific molecule is or comprises SEQ ID NO:10. In further embodiments, the bi-specific molecule that consists of or comprises SEQ ID NO:10 is isolated.

Pharmaceutical Composition

In another aspect, the disclosure provides a pharmaceutical composition comprising the bi-specific molecule described herein. The pharmaceutical composition can also comprise pharmaceutically acceptable carriers, stabilizers, excipients, and other additives to provide an appropriate formulation for the preferred route of administration, as is familiar in the art. These additional additives are typically designed to avoid affecting the biological activity or availability of the bi-specific molecule.

In other embodiments, pharmaceutical compositions of the present disclosure can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

Generally, the pharmaceutical composition is formulated for appropriate systemic administration, such as oral or injection (e.g., subdermal) administration. However, other routes of administration are commonly used and are also encompassed herein.

Nucleic Acids, Vectors, Cell-Expression Systems

In another aspect, the disclosure provides a nucleic acid encoding polypeptide components of the bi-specific molecule described above. In embodiments where the bi-specific molecule is a fusion protein (e.g., all components are polypeptide joined in a single polymer), the nucleic acid can encode the entire fusion protein.

As used herein, the term "nucleic acid" refers to any polymer molecule that comprises multiple nucleotide subunits (i.e., a polynucleotide). Nucleic acids encompassed by the present disclosure can include deoxyribonucleotide polymer (DNA), ribonucleotide polymer (RNA), cDNA or a synthetic nucleic acid known in the art.

Nucleotide subunits of the nucleic acid polymers can be naturally occurring or artificial or modified. A nucleotide typically contains a nucleobase, a sugar, and at least one phosphate group. The nucleobase is typically heterocyclic. Canonical nucleobases include purines and pyrimidines and more specifically adenine (A), guanine (G), thymine (T) (or typically in RNA, uracil (U) instead of thymine (T)), and cytosine (C). The sugar is typically a pentose sugar. Suitable sugars include, but are not limited to, ribose and deoxyribose. The nucleotide is typically a ribonucleotide or deoxyribonucleotide. The nucleotide typically contains a monophosphate, diphosphate, or triphosphate. These are generally referred to herein as nucleotides or nucleotide residues to indicate the subunit. Without specific identification, the general terms nucleotides, nucleotide residues, and the like, are not intended to imply any specific structure or identity. The nucleotides can also be synthetic or modified.

In another aspect, the disclosure provides vectors comprising the nucleic acid sequences described herein, such as a vector comprising a nucleic acid sequence encoding the polypeptide described above. Such vectors are useful for the recombinant expression of the fusion protein in a cell-based expression system. Such expression systems are well-known in the art, and include cell strains optimized for recombinant expression of genes associated with specific vector parameters. For example, any vector described herein can further comprise a promoter sequence to facilitate expression of the nucleic acid encoding the fusion protein in the intended cellular expression system. Any appropriate promoter can be used, such as a constitutive promoter or inducible promoter, appropriate for the expression system to be used, as known in the art. For example, an inducible promoter can comprise an acetamide-inducible promoter. Additionally, the vector can also include selectable markers, such as antibiotic or toxin resistance genes, that will confer protection against such applied agents. In this manner, cells that are successfully transformed with the operational vector can be retained in culture and the non-transformed cells in the system can be removed.

Also provided are cultured cells transfected with any vector described herein, or progeny thereof, wherein the cell is capable of expressing a protein, e.g., fusion protein, as described above. The cell can be prokaryotic, such as *E. coli*, or eukaryotic, such as yeast, arthropod, or mammalian.

Methods

The disclosed bi-specific molecule has a variety of applications. As described, a significant advantage is the ability to confer target-cell specificity in the modulation (i.e., inhibition) of Notch signaling. The bi-specific molecule is specifically conferred by the choice of a high affinity cell-targeting domain that specifically binds antigen that is characteristic of the target cell. Thus, the bi-specific molecule can be administered to a heterogeneous population of cells, such as in vivo in a complex organism or in vitro in a culture.

Accordingly, in one aspect, the disclosure provides a method for modulating (e.g., inhibiting) Notch signaling in a cell-type of interest, the method comprising contacting a population of cells comprising the cell-type of interest with an effective amount of the disclosed bi-specific molecule. Similarly, in another aspect, the disclosure provides a method for inhibiting Notch-dependent development in a cell type of interest, comprising contacting a heterogeneous population of cells comprising the cell-type of interest with an effective amount of the disclosed bi-molecule. The heterogeneous population of cells can be in vivo in a living organism or in vitro/ex vivo in a culture. In some scenarios, the heterogeneous population of cells comprises a plurality of similar cells (i.e., derived from the same origin or source) but which are at different stages of development and differentiation. The application of the amount of the disclosed bi-specific molecule can provide a homogenizing influence on the population of cell-type of interest, which all express the same characteristic antigen, but may be at different stages of development or differentiation. This allows the members of this population reset to the same phase of (non)differentiation to provide a more homogenized population.

The methods of these aspects can be useful, for example, for expansion and manipulation of a population of cells, such as stem cells or progeny cells with some degree of differentiation along a developmental lineage, as obtained from a subject. For example, in some instances, the disclosed methods and compositions can be applied to ex vivo stem cell (or progeny cell) production and/or engineering. In this regard, administration of stem cells or progeny cells with some degree of differentiation can be therapeutically beneficial for a variety of medical conditions where the extant population of functional cells is deficient in some way. For example, donor stem cells, such as from umbilical cord blood, can be cultured for eventual administration. However, the initially obtained population of stem cells, while reflecting a "cell-type of interest," may still be rather heterogeneous, reflecting various stages of quiescence and differentiation. Because it is desirable to confer desired characteristics on the ex vivo population en masse and/or expand the relevant ex vivo sub-population of isolated cells to sufficient numbers for administration, the application of the disclosed methods and compositions to the initial ex vivo population can prevent premature development and differentiation of the cells that are further advanced towards certain end-points. Accordingly, the resulting population exhibits greater homogeneity in its quiescence, or stages of differentiation, which makes it amenable to more uniform expansion and/or potential manipulation into a preferred developmental lineage. Persons of ordinary skill in the art can readily apply this approach as part of a method to produce expanded populations of desired stem or other progenitor cells in ex vivo cultures. The culture can then be rationally and more uniformly guided along a desired developmental lineage for various therapeutic applications using known culturing conditions and growth factors for that purpose. For example, the disclosed compositions and methods can be applied as part of an approach to homogenize and expand ex vivo cultures of progenitor cells, e.g., hematopoietic stem cells (HSC), which can be rationally differentiated various desired progeny lineages, such as T-cell precursors, T-cell subsets, dendritic cells, NK cells, and the like, using known growth/developmental factors. For example, see Delaney, C., et al., "Notch-mediated expansion of human cord blood progenitor cells capable of rapid myeloid reconstitution," *Nature Medicine* 16(2):232-237 (2010), incorporated herein by reference in its entirety, which describes a similar approach to generating an ex vivo population of CD34+ progenitor cells with enhanced myeloid engraftment characteristics. See also WO/2015/187815, WO/2013/086436, which address expanding and selectively differentiating progenitor cells using modulation of Notch signaling, each of which is incorporated herein by reference in its entirety. The role of Notch signaling in development and regulation of the immune system, including T-cell development is the focus of investigations, see, e.g., Radtke F., et al., "Regulation of innate and adaptive immunity by Notch," *Nature Review Immunology* 13:427-437 (2013), and Taghon, T., et al., (2012), "Notch signaling during human T cell development," Radtke, F. (Ed.), Chapter 4 in Notch Regulation of the Immune System, Vol. 360 of the series Current Topics in Microbiology and Immunology, pgs. 75-97, Springer Berlin Heidelberg, each incorporated herein by reference in its entirety. As indicated above, it will be appreciated that such approaches are not necessarily limited to just stem cells or stem cells of a certain type, but can be applied to obtaining, homogenizing, expanding, and/or further differentiating any type of stem cell or cell already differentiated to some degree along a defined developmental path or lineage.

Because the cell-type of interest is specifically (or preferentially) targeted, it will be appreciated that the above applications can also be modified for in vivo methods for modulating (e.g., inhibiting) Notch signaling in an entire cell-population of interest. This can be applied in efforts to homogenize, expand, and ultimately differentiate a progenitor cell type of interest to produce higher levels of progeny cells in a particular developmental lineage.

Determination of Notch modulation can be performed according to any established method indicative of Notch signaling. For example, determination of Notch modulation, either increased or decreased signaling, can be performed by monitoring relative or absolute levels of downstream gene products resulting from Notch activation. An illustrative, non-limiting example of a relevant downstream product is Hes1. Descriptions of monitoring downstream Hes1 levels to assess Notch signaling are provided in more detail below. Alternatively, reporter systems are available to indicate Notch signaling, such as the CHO-K1 Notch reporter system. See, e.g., Sprinzak, D., et al., "Cis-interactions between Notch and Delta generate mutually exclusive signalling states," *Nature* 465(7294):86-90 (2010), incorporated herein by reference in its entirety. Thus, in some embodiments, Notch modulation, e.g., inhibition, is determined by a reporter CHO-K1 Notch reporter system or by assessing a change in a downstream signaling factor, such as Hes1. In some embodiments, the change assessed is significant compared to control.

In another aspect, the disclosure provides a method for inhibiting the development of a cancer cell or cancer progenitor cell, comprising contacting the cancer cell or cancer progenitor cell with the disclosed bi-specific molecule. In the context of the bi-specific molecule as described above, the cancer cell or cancer progenitor cell in this method is the cell-type of interest and the cell-targeting domain specifically binds to an antigen characteristic of the cancer cell or cancer progenitor cell.

The term "inhibiting the development of a cancer or cancer progenitor cell" refers to slowing, suspending, or stopping the transformation, reproduction, or differentiation of the cancer cell or cancer progenitor cell relative to similar conditions where the bi-specific molecule are not contacted to the cell.

The method of this aspect is applicable to any cancer cell where Notch plays a functional role in initiation, maintenance, resistance, and/or progression of the cancer. In many case, the role of Notch is resultant of its enhanced, or dysregulated, signaling in the cells. Such cancers are described in more detail above, although some non-limiting examples of the cancer cell include T (leukemic) cell, breast cancer cell, prostate cell, lung cancer cell, glioblastoma, colo-rectal cancer cell, cervical cancer cell, melanoma cancer cell, pancreatic cancer cell, esophageal cancer cell, and the like, or a progenitor of any of the foregoing.

The method of this aspect can be applied in vitro, for example, in a biopsy sample obtained from a subject with cancer. In vitro applications can include scenarios where the sample is being tested for the presence of cancer or tested for the responsiveness to Notch-based intervention. In other embodiments, the cancer cell is in vivo in a subject with the cancer and the amount of bi-specific molecule is administered to the subject.

The bi-specific molecule can also be applied in a method of treating or inhibiting cancer in a subject in need thereof. Such method comprises administering a therapeutically effective amount of the bi-specific molecule, such as in a pharmaceutical composition as described above, to the subject. Again, the cancer cell or cancer progenitor cell in the subject is the cell-type of interest and the cell targeting domain of the molecule specifically binds to an antigen characteristic of the cancer cell or cancer progenitor cell.

The bi-specific molecule can be designed for any particular cell-type of interest by the selection of the antigen characteristic of the cell-type of interest and the corresponding cell-targeting domain to be incorporated into the bi-specific molecule. Cancer cells applicable in this method are described elsewhere herein. In a specific and illustrative embodiment, the subject has leukemia and the cell targeting domain of the bi-specific molecule specifically binds to CD33.

The bi-specific molecule can be formulated and dosed for any appropriate route of administration. Furthermore, the administration of the bi-specific molecule, or a pharmaceutical composition containing the same, can also be administered in combination with other therapeutic interventions, including other anti-cancer therapeutics. In certain embodiments, at least one additional therapeutic and the disclosed bi-specific molecule as disclosed herein are administered concurrently to a subject. When administered in combination, each component can be administered at the same time or sequentially in any order at different points in time. Thus, each component can be administered separately but sufficiently closely in time so as to provide the desired therapeutic effect. Such additional therapeutic agents can be cytotoxic agents that further inhibit or treat the cancer. Many such agents are known. Nonlimiting examples include aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, duocarmycin, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol™), pilocarpine, prochloroperazine, rituximab, saproin, tamoxifen, taxol, topotecan hydrochloride, trastuzumab, vinblastine, vincristine, vinorelbine tartrate, and the like.

While much of this disclosure addresses the dysregulation of Notch in cancers, it will be appreciated that dysregulation of Notch plays a role in other, non-cancerous diseases. Thus, it is also desirable to address dysregulation in specific cell-types for such non-cancerous diseases. Accordingly, in yet another aspect, the disclosure provides a method of treating a disease treatable by inhibiting Notch signaling in a cell-type of interest, comprising administering a therapeutically effective amount of the bi-specific molecule, or a pharmaceutical composition containing the same, as disclosed herein. Illustrative, non-limiting examples of such other diseases include spondylocostal dysostoses, Alagille syndrome, Hajdu-Cheney syndrome, Alzheimer disease, cerebral autosomal dominant arteriopathy with subcortical infarcts, aortic valve disease, and leukoencephalopathy. As described herein, the specific targeting of the bi-specific molecule requires the incorporation of cell-targeting domain that specifically binds to an antigen characteristic of the altered or diseased cell type. Many characteristic antigens are known or readily discoverable, and are thus encompassed by the present disclosure through the application of ordinary skill in the art.

As used herein, the terms "treatment," "treating," and the like, refer to administering the bi-specific molecule for the purposes of obtaining an effect. The effect can be prophylactic in terms of completely or partially preventing a disease or symptom thereof and/or can be therapeutic in terms of achieving a partial or complete cure for a disease and/or symptoms of the disease. "Treatment," as used herein, can include treatment of a cancer and/or tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease); (b) inhibiting the disease, i.e., arresting its development; (c) preventing recurrence of the disease; and (d) relieving the disease, i.e., causing regression of the disease.

The term "subject" as used above in reference to the methods can refer to any animal with the target cell-type of interest. Subjects are typically mammals, and can include the non-limiting examples of primates (including, e.g., human, monkey, and the like), rodent (including, e.g., rat, mouse, guinea pig, and the like), dog, cat, horse, cow, pig, sheep, and the like. In some embodiments, the subject is a human subject with cancer.

Additional Definitions

Unless specifically defined herein, all terms used herein have the same meaning as they would to one skilled in the art of the present invention. Practitioners are particularly directed to Sambrook J., et al. (eds.), *Molecular Cloning: A Laboratory Manual*, 3rd ed., Cold Spring Harbor Press, Plainsview, N.Y. (2001); Ausubel, F. M., et al. (eds.), *Current Protocols in Molecular Biology*, John Wiley & Sons, New York (2010); and Coligan, J. E., et al. (eds.), *Current Protocols in Immunology*, John Wiley & Sons, New York (2010) for definitions and terms of art.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words "comprise," "comprising," and the like, are to be construed in an inclusive sense as opposed to an exclusive or exhaustive sense; that is to indicate, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application.

"Percent sequence identity" or grammatical equivalents means that a particular sequence has at least a certain percentage of amino acid residues identical to those in a specified reference sequence using an alignment algorithm. An example of an algorithm that is suitable for determining sequence similarity is the BLAST algorithm, which is described in Altschul, et al., *J. Mol. Biol.* 215:403-410 (1990). Software for performing BLAST analyses is publicly available through the National Center for Biotechnology Information (NCBI) website.

The term "wildtype," "wild-type," "WT" and the like refers to a naturally-occurring polypeptide or nucleic acid sequence, i.e., one that does not include a man-made variation.

The terms "subject," "individual," and "patient" are used interchangeably herein to refer to a mammal being assessed for treatment and/or being treated. In certain embodiments, the mammal is a human. The terms "subject," "individual," and "patient" encompass, without limitation, individuals having cancer. Subjects may be human, but also include other mammals, particularly those mammals useful as laboratory models for human disease, e.g., mouse, rat, dog, non-human primate, etc.

The terms "subject," "individual," and "patient" are used interchangeably herein to refer to a mammal being assessed for treatment and/or being treated. In certain embodiments, the mammal is a human. The terms "subject," "individual," and "patient" encompass, without limitation, individuals having cancer. Subjects may be human, but also include other mammals, particularly those mammals useful as laboratory models for human disease, e.g., mouse, rat, dog, non-human primate, etc.

Treating may refer to any indicia of success in the treatment or amelioration or prevention of a cancer, including any objective or subjective parameter such as abatement; remission; diminishing of symptoms or making the disease condition more tolerable to the patient; slowing in the rate of degeneration or decline; or making the final point of degeneration less debilitating.

The treatment or amelioration of symptoms can be based on objective or subjective parameters; including the results of an examination by a physician. Accordingly, the term "treating" includes the administration of the compounds or agents of the present disclosure to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

As indicated above, certain embodiments of the bi-specific molecule comprise an affinity reagent that serves as the cell-targeting domain and/or the Notch binding domain. In some embodiments, the indicated affinity reagent is an antibody. As used herein, the term "antibody" encompasses antibodies and antibody fragments thereof, derived from any antibody-producing mammal (e.g., mouse, rat, rabbit, and primate including human), that specifically bind to an antigen of interest (e.g., Notch or a cell-type specific antigen). Exemplary antibodies multispecific antibodies (e.g., bispecific antibodies); humanized antibodies; murine antibodies; chimeric, mouse-human, mouse-primate, primate-human monoclonal antibodies; and anti-idiotype antibodies. The antigen-binding molecule can be any intact antibody molecule or fragment thereof (e.g., with a functional antigen-binding domain).

An antibody fragment is a portion derived from or related to a full-length antibody, preferably including the complementarity-determining regions (CDRs), antigen binding regions, or variable regions thereof. Illustrative examples of antibody fragments and derivatives useful in the present disclosure include Fab, Fab', F(ab)$_2$, F(ab')$_2$ and Fv fragments, nanobodies (e.g., V$_H$H fragments and V$_{NAR}$ fragments), linear antibodies, single-chain antibody molecules, multi-specific antibodies formed from antibody fragments, and the like. Single-chain antibodies include single-chain variable fragments (scFv) and single-chain Fab fragments (scFab). A "single-chain Fv" or "scFv" antibody fragment, for example, comprises the V$_H$ and V$_L$ domains of an antibody, wherein these domains are present in a single polypeptide chain. The Fv polypeptide can further comprise a polypeptide linker between the V$_H$ and V$_L$ domains, which enables the scFv to form the desired structure for antigen binding. Single-chain antibodies can also include diabodies, triabodies, and the like. Antibody fragments can be produced recombinantly, or through enzymatic digestion.

The above affinity reagent does not have to be naturally occurring or naturally derived, but can be further modified to, e.g., reduce the size of the domain or modify affinity for the Notch (or cell-specific antigen) as necessary. For example, complementarity determining regions (CDRs) can be derived from one source organism and combined with other components of another, such as human, to produce a chimeric molecule that avoids stimulating immune responses in a subject.

Production of antibodies or antibody-like molecules can be accomplished using any technique commonly known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual* (Cold Spring Harbor Laboratory Press, 2nd ed. 1988); Hammerling et al., in: *Monoclonal Antibodies and T-Cell Hybridomas* 563-681 (Elsevier, N.Y., 1981), incorporated herein by reference in their entireties. The term "monoclonal antibody" refers to an antibody that is derived from a single clone, including any eukaryotic, prokaryotic, or phage clone, and not the method by which it is produced. Methods for producing and screening for specific antibodies using hybridoma technology are routine and well known in the art. Once a monoclonal antibody is identified for inclusion within the bi-specific molecule, the encoding gene for the relevant binding domains can be cloned into an expression vector that also comprises nucleic acids encoding the remaining structure(s) of the bi-specific molecule.

Antibody fragments that recognize specific epitopes can be generated by any technique known to those of skill in the art. For example, Fab and F(ab')$_2$ fragments of the invention can be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CHI domain of the heavy chain. Further, the antibodies of the present invention can also be generated using various phage display methods known in the art.

As used herein, the term "aptamer" refers to oligonucleic or peptide molecules that can bind to specific antigens of interest. Nucleic acid aptamers usually are short strands of oligonucleotides that exhibit specific binding properties. They are typically produced through several rounds of in vitro selection or systematic evolution by exponential enrichment protocols to select for the best binding properties, including avidity and selectivity. One type of useful nucleic acid aptamers are thioaptamers, in which some or all of the non-bridging oxygen atoms of phophodiester bonds have been replaced with sulfur atoms, which increases binding energies with proteins and slows degradation caused by nuclease enzymes. In some embodiments, nucleic acid aptamers contain modified bases that possess altered side-chains that can facilitate the aptamer/target binding.

Peptide aptamers are protein molecules that often contain a peptide loop attached at both ends to a protamersein scaffold. The loop typically has between 10 and 20 amino acids long, and the scaffold is typically any protein that is soluble and compact. One example of the protein scaffold is Thioredoxin-A, wherein the loop structure can be inserted within the reducing active site. Peptide aptamers can be generated/selected from various types of libraries, such as phage display, mRNA display, ribosome display, bacterial display and yeast display libraries.

Disclosed are materials, compositions, and components that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the subject matter for which they are cited are hereby specifically incorporated by reference in their entireties.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed.

These examples describe the construction and characterization of an illustrative bi-specific molecule that is shown to specifically target the bi-specific molecule to CD33+ leukemic cells, allowing cell-specific Notch modulation. Specifically, a fusion protein incorporating a single chain, variable fragment directed against the CD33 antigen fused with a high affinity variant (E12) of the extracellular domain of the Notch ligand Delta-like ligand 4 (DLL4). These studies revealed that this fusion protein inhibited Notch activation by immobilized ligand only when the target cells expressed the CD33 antigen and establish cell-type specific modulation of Notch signaling using, e.g., a high affinity antibody component to selectively deliver a Notch-binding modifier, here Notch ligand DLL4-E12. This inhibitory construct is readily amenable to include a binding (e.g., antibody-based) component specific to any desired cell antigen such that can target the bi-specific molecule to the target of interest, and a Notch ligand with specificity for one or more Notch receptors co-expressed by the targeted cell.

Example 1

Construction of the Bi-Specific $DLL4_{e12}$-αCD33 scFv Fusion Molecule.

An expression vector based on pAcGp67A, a baculovirus transfer vector (BD Biosciences, cat. no. 554756) was created to include BamHI and NotI restriction sites in the cloning site and encoded affinity tags, as described below. The vector was used to combine nucleic acids encoding (1) the extracellular domain (ECD) of rat DLL4, E12 variant ($DLL4_{E12}$), (2) a 10 amino acid residue linker consisting of 5× repeats of the sequence Gly-Ser, and (3) a single-chain variable fragment of an anti-CD33 single-chain variable fragment (scFv). The pAcGp67A also provides a C-terminal c-Myc epitope and 8×His tag in the resulting expressed protein.

The ECD of rat DLL4 was encoded to specifically contain mutations G28S, F107L, N118I, I143F, H194Y, L206P, K215E from the wild-type sequence. The full wild-type sequence with the reference amino acid positions is set forth herein as SEQ ID NO: 1. The $DLL4_{E12}$ variant E12 was specifically generated and described in Luca, V. C., et al., "Structural Basis for Notch1 Engagement of Delta-Like 4," Science 347(6224):847-853 (2015), which is incorporated herein in its entirety, as having enhanced affinity for the Notch receptor as compared to wild-type DLL4. An amino acid sequence reflecting the MNNL to EGF2 region (i.e., corresponding to amino acid positions 27 to 283 of SEQ ID NO:1), of the $DLL4_{E12}$ variant is set forth herein as SEQ ID NO:2. However, it is noted that the above-indicated mutations are with respect to the position in SEQ ID NO:1.

The encoded single-chain variable fragment of an anti-CD33 single-chain variable fragment (scFv) has an amino acid sequence set forth herein as SEQ ID NO:9. The encoded anti-CD33 scFv itself is composed of a variable heavy ($V_H$) domain linked to a variable light ($V_L$) domain by a 15 amino acid residue linker with 3× repeats of the sequence Gly-Gly-Gly-Gly-Ser. The full length bi-specific $DLL4_{E12}$-αCD33 scFv fusion molecule had the amino acid sequence set forth as SEQ ID NO:10.

The bi-specific fusion protein was expressed using baculovirus by infecting 1 L of Hi-Five cells (Invitrogen) from *Trichoplusia ni* at a density of 2×10⁶ cells/mL and harvesting cultures after 48 hours. Proteins were purified from supernatants by nickel chromatography. Nickel nitrilotriacetic acid agarose resin (Nickel-NTA, Qiagen) was washed with HEPES buffered saline (HBS: 20 mM HEPES pH 7.4, 150 mM sodium chloride) plus 1 mM calcium chloride and 10 mM imidazole, and protein was eluted with HBS plus 1 mM calcium chloride and 250 mM imidazole. Size-exclusion chromatography was performed in HBS+1 mM calcium chloride on a Superdex-200 column.

A schematic representation of the expressed fusion molecule is provided in FIG. 1A. As illustrated, the $DLL4_{E12}$ domain of the bi-specific molecule represents the extracellular (ED) domain, which is at the N-terminal half of the bi-specific fusion protein, has an N-terminus Notch ligand (MNNL) domain followed by a Delta-Serrate-Lag2 (DSL) domain, followed by eight epidermal growth factor-like (EGF) domain repeats, which is typical for DLL4 ligands.

Additionally, for purposes of control assays, the $DLL4_{E12}$ and anti-CD33 scFv domains were also produced separately, each with a C-terminal c-Myc epitope and 8×His tag, according to the general scheme indicated above. See FIGS. 1B and C, respectively.

Example 2

Characterization of the Cell-Specific Inhibitory Effect of the Bi-Specific $DLL4_{e12}$-αCD33 scFv Fusion Molecule on Notch Signaling.

To characterize the effect of the bi-specific $DLL4_{E12}$-αCD33 scFv fusion molecule on Notch signaling, cells with or without CD33 surface antigen were exposed to a panel of different Notch ligands including the bi-specific $DLL4_{E12}$-αCD33 scFv fusion molecule. First, HL60 (CD33+ human pro-myelocytic leukemia cells) and REH (CD33− human B-cell precursor leukemia cells) were incubated for 4 hours on non-tissue culture wells coated with the following individual immobilized proteins: Delta1$^{ext-IgG}$ ("DLL1"), wild-type Delta4 extracellular domain ("DLL4-ECD"), high-affinity DLL4 extracellular domain variant ("DLL4-E12"), single chain variable fragment to anti-CD33 antibody ("CD33"), the bi-specific high affinity $DLL4_{E12}$-αCD33 scFv fusion molecule ("DLL4-E12/CD33") or control IgG, each at 50 nM. cDNA was generated using RNA isolated from harvested cells. Relative expression of Hes1 is indicated for each culture condition compared to control IgG ($2^{\Delta\Delta Ct}$).

Figure 2A:
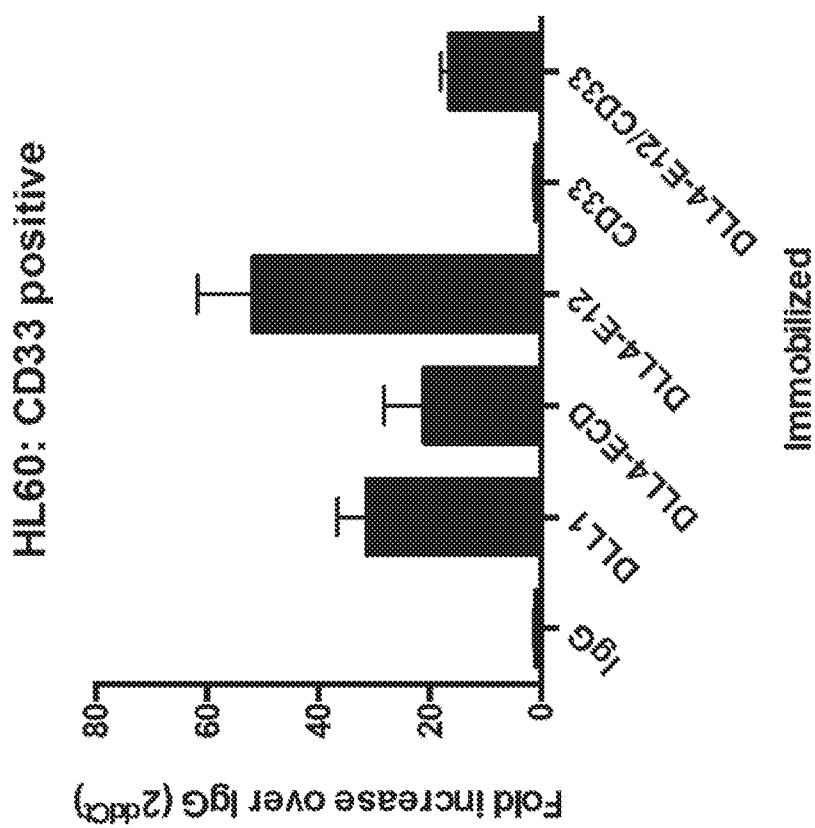

FIG. 2A graphically illustrates the Hes1 expression in CD33+HL60 cells relative to the level induced by non-stimulating IgG control for different (potential) ligands. As illustrated, the bi-specific high affinity $DLL4_{E12}$-αCD33 scFv fusion molecule resulted in a significant decrease in Notch signaling in the CD33+ cells, as determined via Hes1 expression, as compared to the known high affinity agonist $DLL4_{E12}$. FIG. 2B graphically illustrates the Hes1 expression in CD33− REH cells relative to the level induced by non-stimulating IgG control for different (potential) ligands. In contrast to the CD33+ cells, these CD33− REH cells had comparable Notch signaling when exposed to either the bi-specific $DLL4_{E12}$-αCD33 scFv fusion molecule or the high affinity agonist $DLL4_{E12}$ without the cell-targeting domain. These results demonstrate that the inclusion of a targeting domain (i.e., CD33) in a fusion protein with the Notch ligand results in relative reduction of Notch signaling in cells containing the antigen targeted by the targeting domain.

Figure 3:
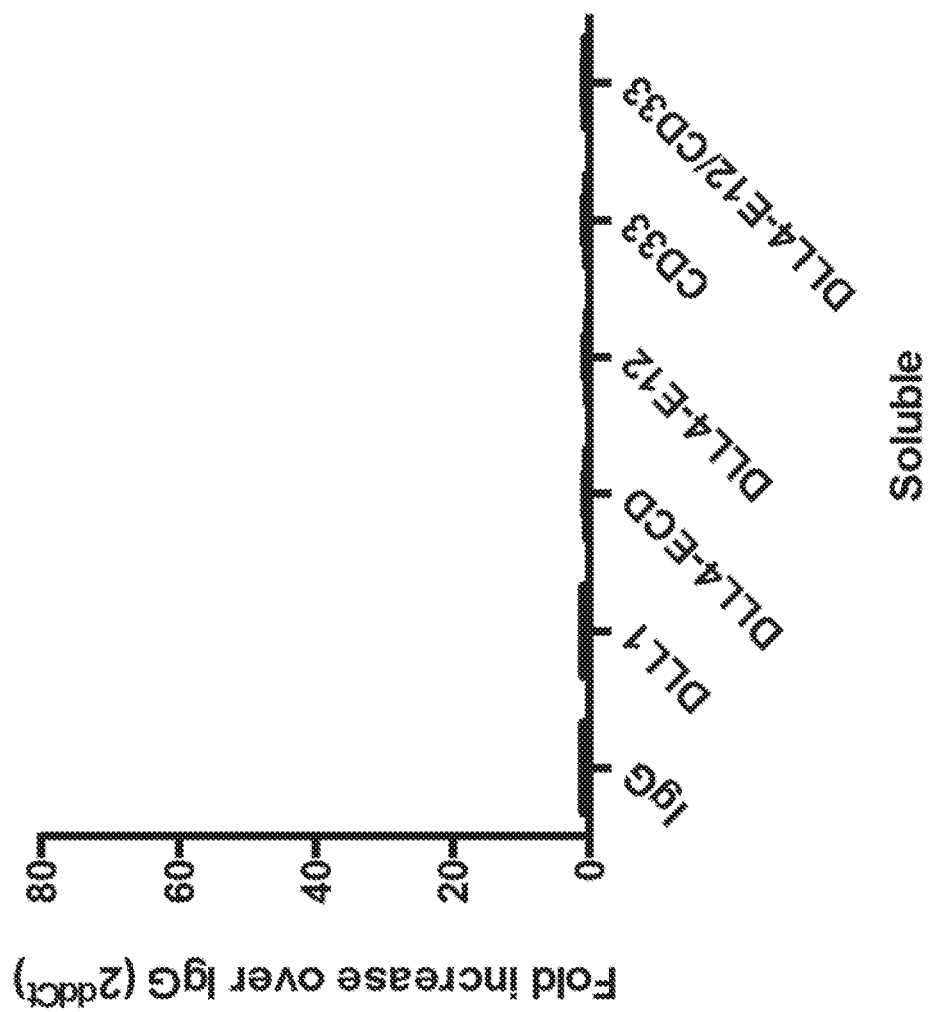
FIG. 3 graphically illustrates (lack of) Notch signaling induced by the bi-specific $DLL4_{E12}$-αCD33 scFv, and other known agonist ligands, when presented in soluble form. Notch signal levels are the relative Hes1 transcription levels in the CD33+HL60 cells when exposed to soluble ligands.

Next, Notch signaling was investigated when the CD33+ HL60 cells were exposed to the same Notch ligands described above in soluble, not immobilized, form. Specifically, the CD33+HL60 cells were incubated for 4 hrs on non-tissue culture wells in the presence of 50 nM of each soluble agonist (indicated in FIG. 3 as DLL1, DLL4-ECD, DLL4-E12, CD33, or DLL4-E12/CD33, with IgG as control). As above, cDNA was generated using RNA isolated from harvested cells. Relative expression of Hes1 is reported for each culture condition compared to control IgG ($2^{\Delta\Delta Ct}$) as an indicator of Notch signaling. As illustrated in FIG. 3, none of the ligands stimulated Notch signaling when in soluble form. This demonstrates that Notch signaling for the Notch ligands is dependent on their immobilization. Without being held to any particular theory, this likely reflects the requirement that the ligand produces a conformational change in the Notch receptor via a mechanical "tug" to induce signaling. Such a mechanical "tug" is likely not sufficiently provided when the ligand is soluble and lacking an anchor in another structure. Interestingly, the soluble bi-specific $DLL4_{E12}$-αCD33 scFv fusion molecule has the opportunity to bind to the target cell's own CD33 surface antigens, but still failed to induce Notch signaling.

Considering that the immobilized bi-specific $DLL4_{E12}$-αCD33 scFv fusion molecule reduced the relative Notch signaling in CD33+ cells compared to CD33− cells, but the soluble form of the bi-specific fusion molecule did not induce any Notch signaling in the same cells, it was investigated whether the soluble bi-specific $DLL4_{E12}$-αCD33 scFv fusion molecule could inhibit Notch signaling, i.e., perform as an antagonist, in a targeted and cell-specific manner. CD33+HL60 cells or CD33− REH cells were incubated for 4 hrs on non-tissue culture wells coated with 50 nM immobilized IgG (as control) or $DLL4_{E12}$ ligand ("DLL4-E12"; an established high affinity agonist). The incubation was in the presence of 50 nM soluble IgG, soluble $DLL4_{E12}$ ligand, or soluble control IgG. As above, cDNA was generated using RNA isolated from harvested cells. Relative expression of Hes1 is reported for each culture condition compared to control IgG ($2^{\Delta\Delta Ct}$) as an indicator of Notch signaling.

Figure 4B:
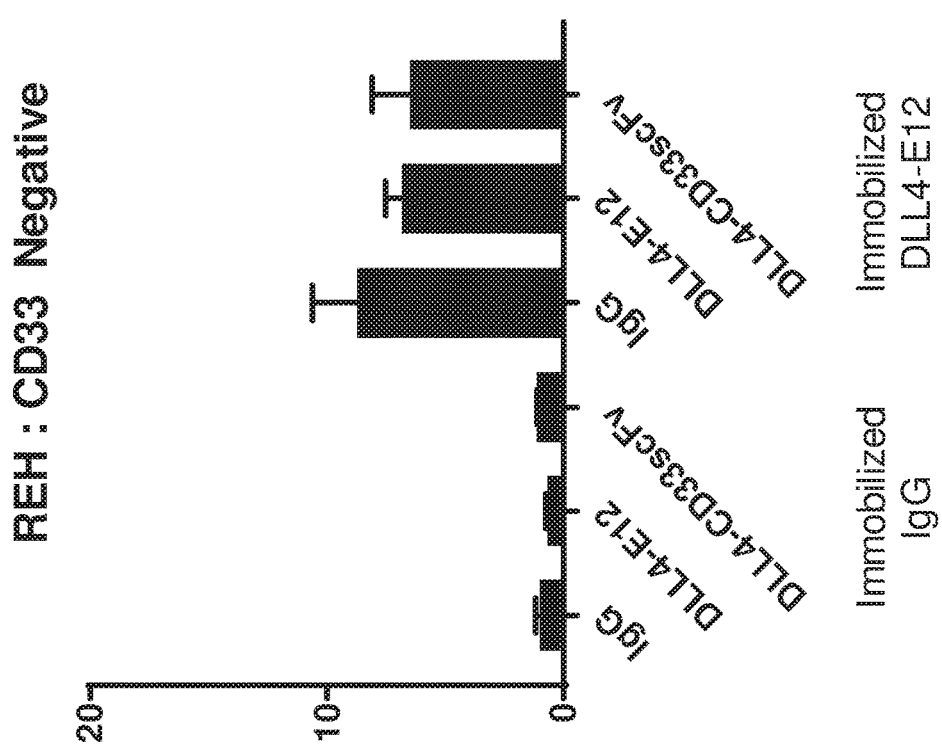
FIGS. 4A and 4B graphically illustrate the effects of the soluble bi-specific $DLL4_{E12}$-αCD33 scFv fusion molecule on Notch signaling in target cells when the cells are exposed to established Notch agonist.
Figure 4A:
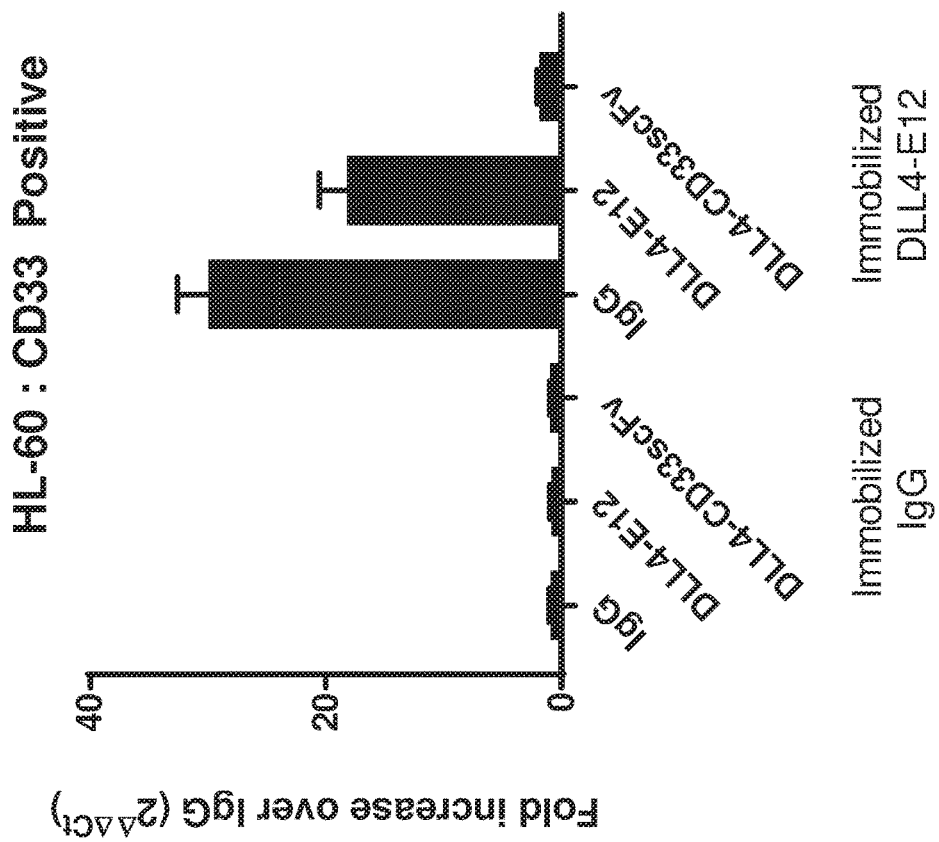
Figure 5:
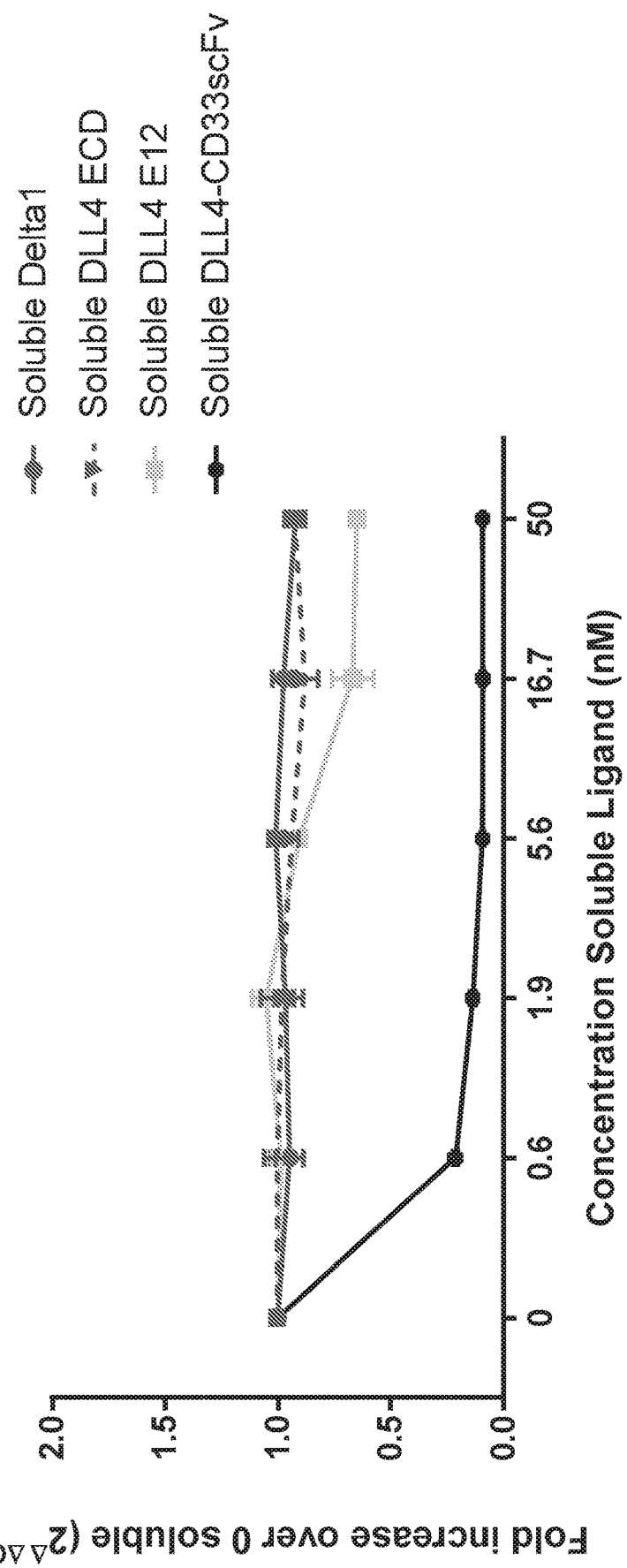
FIG. 5 graphically illustrates the dose dependent inhibition of Notch signaling by the soluble bi-specific DLL4$_{E12}$-αCD33 scFv fusion molecule, demonstrating that low doses (less than 1 nM) of the bi-specific molecule effectively inhibit Notch activation by a high affinity ligand.
Figure 6:
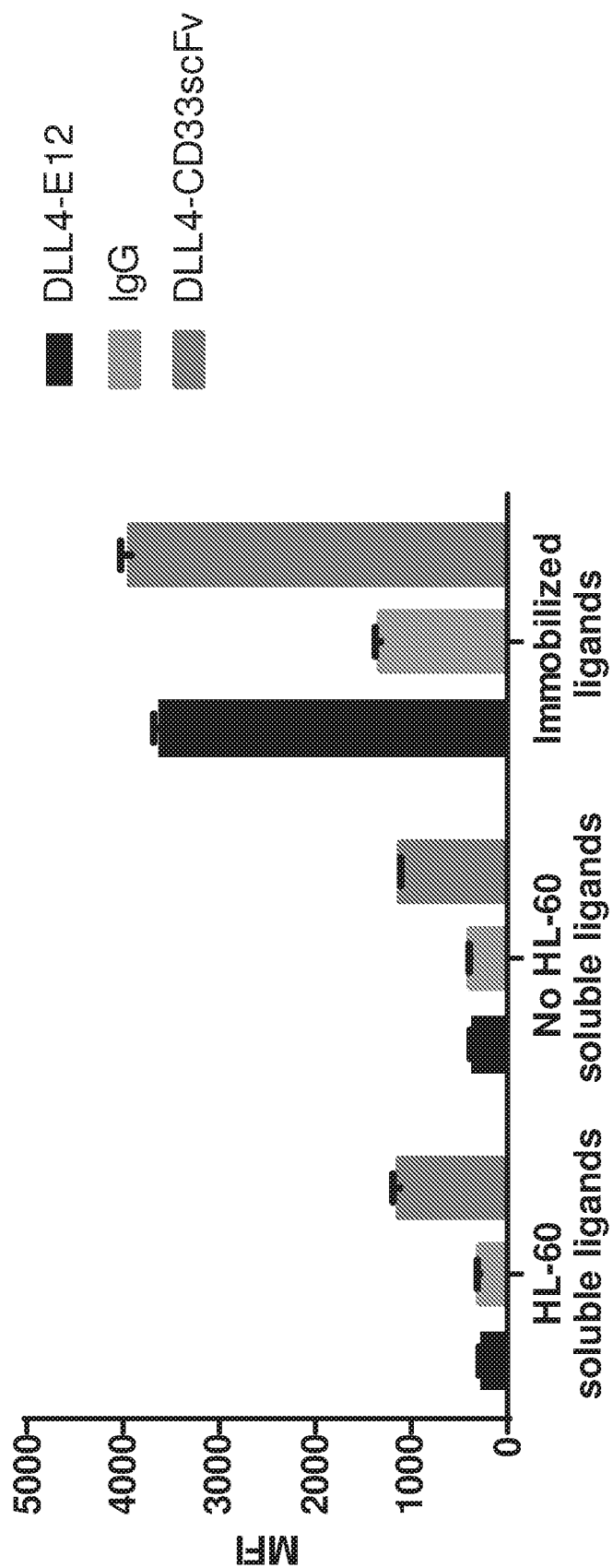
FIG. 6 graphically illustrates the Notch activation in the CHO-K1 Notch reporter system when incubated with or without CD33+HL60 cells and various soluble ligands. Immobilized ligands were also tested for control. Notch activation was ascertained by YFP expression in the CHO-K1 cells by flow cytometry as a function of mean fluorescence intensity (MFI).
Figure 7:
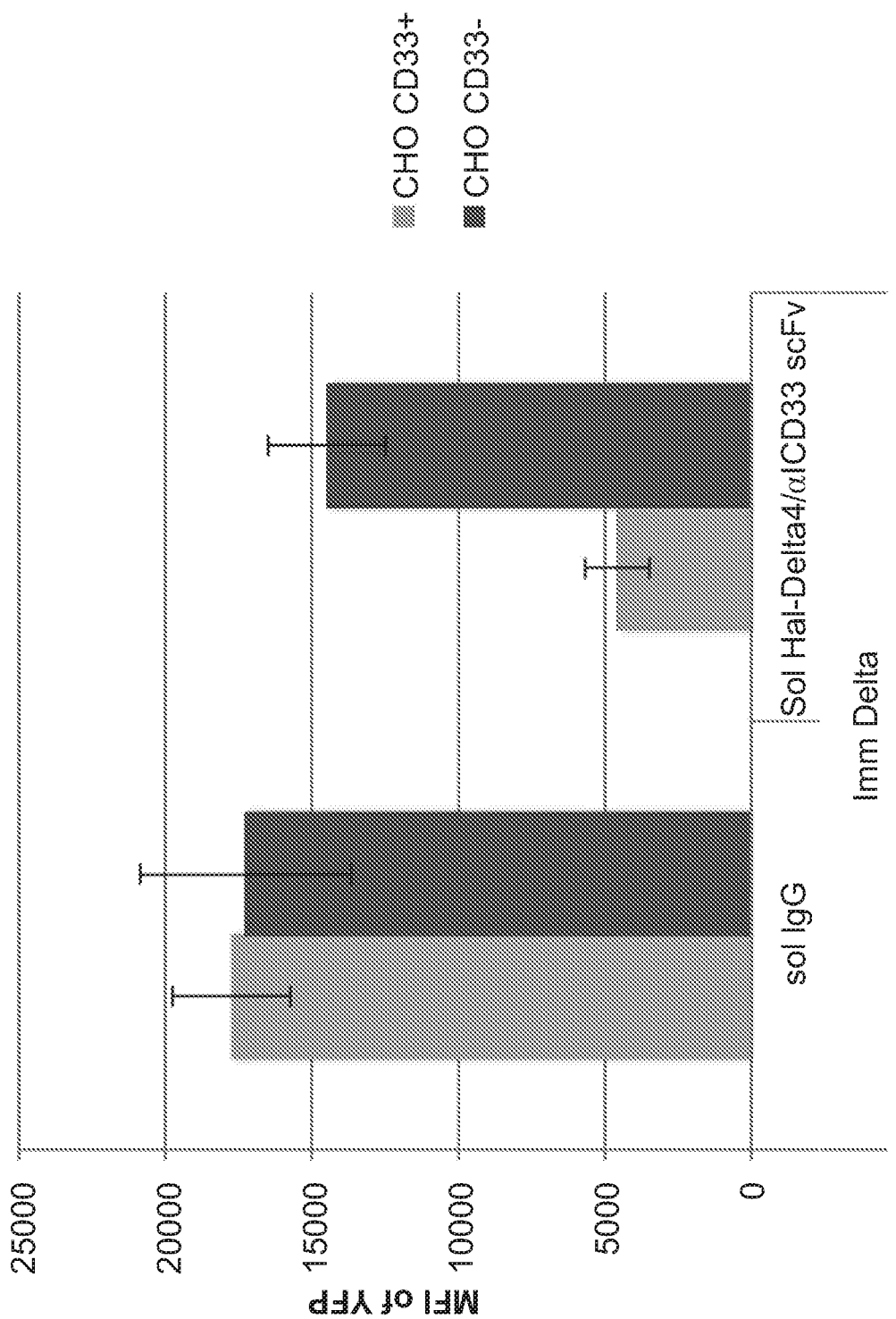
FIG. 7 graphically illustrates the specific inhibition of Notch activation by soluble bi-specific DLL4$_{E12}$-αCD33 scFv fusion molecule in CHO cells with CD33 expression. A mixed cell population of CHO cells with or without CD33+ expression was exposed to immobilized Notch ligand in the presence of IgG control or the soluble bi-specific DLL4$_{E12}$-αCD33 scFv. Notch activation was ascertained by YFP expression in the CHO-K1 cells by flow cytometry as a function of mean fluorescence intensity (MFI).

As illustrated in FIG. 4A the presence of soluble bi-specific $DLL4_{E12}$-αCD33 scFv fusion molecule drastically reduced and almost completely eliminated Notch signaling by immobilized $DLL4_{E12}$ ligand. In contrast, the presence of soluble DLL4E12 ligand, which lacked a CD33+ targeting domain, only resulted in a modest reduction in Notch signaling levels caused by the immobilized agonist as compared to the irrelevant soluble IgG control. FIG. 4B indicates that for cells lacking the CD33+ targeting antigen, the soluble bi-specific $DLL4_{E12}$-αCD33 molecule (and soluble $DLL4_{E12}$ ligand without a targeting domain) resulted in comparable Notch signaling caused by the immobilized Notch ligand as the irrelevant soluble control IgG. This establishes that the soluble bi-specific $DLL4_{E12}$-αCD33 fusion molecule provides Notch antagonist functionality in a cell-specific manner, i.e., only for target cells that exhibit the relevant cell surface antigen corresponding to the cell-targeting domain of the bi-specific fusion molecule.

Further investigations were conducted to characterize the ability of the soluble bi-specific molecule to prevent or inhibit Notch signaling in target cells.

FIG. 5 illustrates the results of a dosing assay where CD33+HL60 cells were incubated for 4 hrs on non-tissue culture wells coated with 50 nM immobilized high affinity $DLL4_{E12}$ ligand in the presence of increasing doses soluble Delta1, DLL4-ECD, $DLL4_{E12}$, or $DLL4_{E12}$-αCD33 fusion molecule. As above, cDNA was generated using RNA isolated from harvested cells. Relative expression of Hes1 is reported for each culture condition compared to control with no soluble ligand ($2^{\Delta\Delta Ct}$) as an indicator of Notch signaling. As illustrated, a significant inhibition of Notch signaling by the immobilized high affinity ligand was observed at the initial level of 0.6 nM $DLL4_{E12}$-αCD33 fusion molecule. In contrast, the other soluble agents maintained a consistent lack of inhibition over all doses, with the exception of soluble high affinity ligand $DLL4_{E12}$, which lacks a cell-targeting domain. This soluble ligand exhibited only a slight decrease in Notch activation by the immobilized ligand at high doses. This data further establishes that the inclusion of the cell-targeting domain, e.g., the anti-CD33 scFv, confers not just cell-specificity but also the inhibiting functionality of an antagonist ligand relative to the target cell.

To further establish the functionality of the soluble $DLL4_{E12}$-αCD33 fusion molecule as a cell-specific antagonist in a more complicated milieu of cells, which is more representative of an in vivo environment, a CHO-K1 Notch reporter system was employed. See, e.g., Sprinzak, D., et al., Nature 465(7294):86-90 (2010), incorporated herein by reference in its entirety. The CHO-K1 Notch reporter system increases YFP expression upon Notch activation and can be quantified by flow cytometry CHO-K1-DLL1 cells were incubated with soluble human high affinity $DLL4_{E12}$ ligand, IgG, or $DLL4_{E12}$-αCD33 fusion molecule, with or without HL-60 cells. As a control, wells were coated with immobilized ligands prior to addition of CHO-K1-DLL1 cells. After 24 hours, cells were harvested and YFP expression assessed by flow cytometry. As illustrated in FIG. 6, none of the soluble ligands, whether with the presence or absence of the CD33+HL60 cells, resulted in Notch signaling above background or non-specific Notch signaling. For comparison, the immobilized Notch ligands, whether with a CD33+ targeting domain or not, induced elevated Notch signaling in the reporter system. It is noted that the immobilized irrelevant IgG control molecule was associated with equivalent background Notch signaling as the soluble $DLL4_{E12}$-αCD33 fusion, further indicating that the fusion molecule fails to enhance relevant Notch activation in off-target cells (i.e., cells not expressing the cell-specific antigen to the cell-targeting domain).

The data demonstrate that the disclosed soluble bi-specific fusion molecule confers antagonistic, Notch inhibition in a cell-specific manner to target cells expressing the surface antigen associated with the cell-targeting domain. Regardless of the elevated affinity of the Notch binding domain, e.g., the $DLL4_{E12}$, this domain does not by itself confer comparable or relevant inhibitory activity to soluble molecules. Accordingly, the inhibitory and cell-specificity is a surprising and synergistic characteristic of the combination of the cell-targeting domain and Notch-binding domain within the same soluble molecule.

Example 3

Further characterization of the cell-specific inhibitory effect of the bi-specific $DLL4_{E12}$-αCD33 scFv fusion molecule on Notch signaling.

As described above in more detail, CHO-K1 cells provides a robust model for assessing Notch signaling through the quantification of YFP expression, which occurs upon activation of Notch. To further address the specificity performance of the above bi-specific reagent in vitro and in vivo, CHO-K1 cells were genetically modified to express the target antigen, human CD33. This permitted the construction of a controlled mixed cell population of CHO-K1 cells that are CD33+ and CD33− in equivalent amounts, but are otherwise equivalent and provide sensitive and reliable quantification of Notch signaling activity. The mixed cell population of CHO-K1 cells with equivalent numbers of CHO CD33+ and CHO CD33− cells was incubated with immobilized Delta (a Notch ligand that elicits Notch signaling) in the presence or absence of soluble bi-specific reagent (HA-Delta4/αCD33 scFv). Notch activation measured after 24 hours by flow cytometry (specifically assessing the Mean Fluorescence Intensity (MFI) of YFP). The resultant Notch activation is illustrated in the graph of FIG. 7. As illustrated, the addition of soluble bi-specific reagent did not affect the level of Notch activation induced by immobilized Delta in CHO-CD33− cells. However, it led to a significant decrease in Notch activation in CHO-CD33+ cells. Standard (uninhibited) Notch activation by immobilized ligand for both the CD33+ and CD33− cells was established using soluble IgG control and shown to be equivalent for each cell type. This data demonstrates that the bi-specific reagent is capable of inhibiting Notch activation in a cell-type specific manner without inducing Notch activation in non-targeted cells.

While the preferred embodiment of the invention has been illustrated and described, it will be appreciated that various changes can be made therein without departing from the spirit and scope of the invention.

The invention claimed is:

1. A bi-specific molecule, comprising:
a cell-targeting domain that specifically binds to CD33; and
a Notch-binding domain comprising the extracellular domain of a Notch receptor ligand that binds to a Notch receptor on a cell-type of interest.

2. The molecule of claim 1, wherein the Notch-binding domain comprises the extracellular domain of a mammalian Notch receptor ligand.

3. The molecule of claim 2, wherein the mammalian Notch receptor ligand is a ligand to a mammalian Notch1, Notch2, Notch3, or Notch4 receptor.

4. The molecule of claim 2, wherein the mammalian Notch receptor ligand is a Delta protein or Jagged protein.

5. The molecule of claim 4, wherein the Delta protein is Delta Like Ligand 1 (DLL1), DLL3, or DLL4, or wherein the Jagged protein is Jagged 1 or Jagged 2.

6. The molecule of claim 2, wherein the mammalian Notch receptor ligand is Dlk1, Dlk2, DNER, EGFL 7, or F3/contactin.

7. The molecule of claim 2, wherein the extracellular domain of the Notch receptor ligand contains one or more mutations from a wild-type extracellular domain of a Notch receptor ligand resulting in enhanced affinity or specificity of the extracellular domain of the Notch receptor ligand to the Notch receptor as compared to the wild-type extracellular domain, and wherein:
the Notch-binding domain comprises an extracellular fragment of Delta Like Ligand 4 (DLL4) that comprises an N-terminus Notch ligand (MNNL) domain, Delta-Serrate-Lag2 (DSL) domain, and epidermal growth factor (EGF) repeats 1-8 and the one or more mutations from wild-type are selected from G28S, M/V43I, P52S, S96I, F107L, N118I, I143F/T, Q146K, S183N, H194Y, L206P, K215E, L223R, and M257K with respect to the amino acid sequence set forth in SEQ ID NO: 1 or a homologous sequence thereto; or
the Notch-binding domain comprises an extracellular fragment of Jagged 1 that comprises an N-terminus Notch ligand (MNNL) domain, Delta-Serrate-Lag2 (DSL) domain, and epidermal growth factor (EGF) repeats 1-8 and the one or more mutations from wild-type are selected from P100H and Q183P with respect to the amino acid sequence set forth in SEQ ID NO: 4 or a homologous sequence thereto.

8. The molecule of claim 1, wherein the cell-targeting domain comprises an antibody, an antibody fragment, an antibody derivative, a DARpin, an aptamer, or a functional domain thereof.

9. The molecule of claim 8, wherein the antibody fragment or antibody derivative is a single-chain antibody, a bispecific antibody, an Fab fragment, an F(ab)$_2$ fragment, a V$_H$H fragment, a V$_{NAR}$ fragment, or a nanobody.

10. The molecule of claim 1, wherein the cell-targeting domain specifically binds to CD33 with an affinity characterized by a dissociation constant ($K_d$) of 50 nM or less.

11. The molecule of claim 1, wherein the cell-type of interest is a cancer cell or cancer progenitor/stem cell.

12. The molecule of claim 11, wherein the cancer cell is a leukemic cell or a progenitor thereof.

13. The molecule of claim 1, wherein the cell-targeting domain and the Notch-binding domain are joined by at least an intervening flexible linker domain.

14. The molecule of claim 1, wherein the molecule is a fusion polypeptide and each of the cell-targeting domain and Notch-binding domain are polypeptides that do not naturally occur together.

15. A nucleic acid encoding the fusion polypeptide of claim 14.

16. A vector comprising the nucleic acid of claim 15.

17. A cultured cell comprising the vector of claim 16.

18. A pharmaceutical composition comprising the molecule of claim 1, or a pharmaceutically acceptable salt thereof, and a pharmaceutically acceptable carrier.

19. The molecule of claim 1, wherein the extracellular domain of the Notch receptor ligand binds to the Notch receptor with an affinity characterized by a dissociation constant ($K_d$) of about 100 nM to about 0.1 nM.

* * * * *

SEQUENCE LISTING

<160> NUMBER OF SEQ ID NOS: 10

<210> SEQ ID NO 1
<211> LENGTH: 685
<212> TYPE: PRT
<213> ORGANISM: Rattus norvegicus

<400> SEQUENCE: 1

```
Met Thr Pro Gly Ser Arg Ser Ala Cys Arg Trp Ala Leu Leu Leu Leu
1               5                   10                  15

Ala Val Leu Trp Pro Gln Arg Ala Ala Gly Ser Gly Ile Phe Gln Leu
            20                  25                  30

Arg Leu Gln Glu Phe Ala Asn Glu Arg Gly Met Leu Ala Asn Gly Arg
        35                  40                  45

Pro Cys Glu Pro Gly Cys Arg Thr Phe Phe Arg Ile Cys Leu Lys His
    50                  55                  60

Tyr Gln Ala Thr Phe Ser Glu Gly Pro Cys Thr Phe Gly Asn Val Ser
65                  70                  75                  80

Thr Pro Val Leu Gly Thr Asn Ser Phe Val Ile Arg Asp Lys Asn Ser
                85                  90                  95

Gly Ser Gly Arg Asn Pro Leu Gln Leu Pro Phe Asn Phe Thr Trp Pro
            100                 105                 110

Gly Thr Phe Ser Leu Asn Ile Gln Ala Trp His Thr Pro Gly Asp Asp
        115                 120                 125

Leu Arg Pro Glu Thr Ser Pro Gly Asn Ser Leu Ile Ser Gln Ile Ile
    130                 135                 140

Ile Gln Gly Ser Leu Ala Val Gly Lys Asn Trp Lys Ser Asp Glu Gln
145                 150                 155                 160

Asn Asn Thr Leu Thr Arg Leu Arg Tyr Ser Tyr Arg Val Val Cys Ser
                165                 170                 175

Asp Asn Tyr Tyr Gly Asp Ser Cys Ser Arg Leu Cys Lys Lys Arg Asp
            180                 185                 190

Asp His Phe Gly His Tyr Glu Cys Gln Pro Asp Gly Ser Leu Ser Cys
        195                 200                 205

Leu Pro Gly Trp Thr Gly Lys Tyr Cys Asp Gln Pro Ile Cys Leu Ser
    210                 215                 220

Gly Cys His Glu Gln Asn Gly Tyr Cys Ser Lys Pro Asp Glu Cys Asn
225                 230                 235                 240

Cys Arg Pro Gly Trp Gln Gly Pro Leu Cys Asn Glu Cys Ile Pro His
                245                 250                 255

Asn Gly Cys Arg His Gly Thr Cys Thr Ile Pro Trp Gln Cys Ala Cys
            260                 265                 270

Asp Glu Gly Trp Gly Gly Leu Phe Cys Asp Gln Asp Leu Asn Tyr Cys
        275                 280                 285
```

```
Thr His His Ser Pro Cys Lys Asn Gly Ser Thr Cys Ser Asn Ser Gly
    290                 295                 300

Pro Arg Gly Tyr Thr Cys Thr Cys Leu Pro Gly Tyr Thr Gly Glu His
305                 310                 315                 320

Cys Glu Leu Glu Leu Ser Lys Cys Ala Ser Asn Pro Cys Arg Asn Gly
                325                 330                 335

Gly Ser Cys Lys Asp His Glu Asn Ser Tyr His Cys Leu Cys Pro Pro
            340                 345                 350

Gly Tyr Tyr Gly Gln His Cys Glu His Ser Thr Leu Thr Cys Ala Asp
        355                 360                 365

Ser Pro Cys Phe Asn Gly Gly Ser Cys Arg Glu Arg Asn Gln Gly Ala
370                 375                 380

Ser Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Thr Cys Arg Cys Arg Pro Gly Phe
            420                 425                 430

Thr Gly Thr His Cys Glu Leu His Ile Ser Asp Cys Ala Arg Ser Pro
        435                 440                 445

Cys Ala His Gly Gly Thr Cys His Asp Leu Glu Asn Gly Pro Val Cys
450                 455                 460

Thr Cys Pro Ala Gly Phe Ser Gly Arg Arg Cys Glu Val Arg Ile Thr
465                 470                 475                 480

Asn Asp Ala Cys Ala Ser Gly Pro Cys Phe Asn Gly Ala Thr Cys Tyr
                485                 490                 495

Thr Gly Leu Ser Pro Asn Asn Phe Val Cys Asn Cys Pro Tyr Gly Phe
            500                 505                 510

Val Gly Ser Arg Cys Glu Phe Pro Val Gly Leu Pro Pro Ser Phe Pro
        515                 520                 525

Trp Val Ala Val Ser Leu Gly Val Gly Leu Val Val Leu Leu Val Leu
530                 535                 540

Leu Val Met Val Ala Val Ala Val Arg Gln Leu Arg Leu Arg Arg Pro
545                 550                 555                 560

Asp Asp Asp Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Leu
        595                 600                 605

Gln Asn His Thr Leu Asp Tyr Asn Leu Ala Pro Gly Phe Leu Gly Arg
610                 615                 620

Gly Ser Thr Pro Gly Lys Tyr Pro His Ser Asp Lys Ser Leu Gly Glu
625                 630                 635                 640

Lys Val Pro Leu Arg Leu His Ser Glu Lys Pro Ala Cys Arg Ile Ser
                645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val
        675                 680                 685

<210> SEQ ID NO 2
<211> LENGTH: 257
```

```
<212> TYPE: PRT
<213> ORGANISM: Rattus norvegicus

<400> SEQUENCE: 2

Ser Gly Ile Phe Gln Leu Arg Leu Gln Glu Phe Ala Asn Glu Arg Gly
1               5                   10                  15

Met Leu Ala Asn Gly Arg Pro Cys Glu Pro Gly Cys Arg Thr Phe Phe
            20                  25                  30

Arg Ile Cys Leu Lys His Tyr Gln Ala Thr Phe Ser Glu Gly Pro Cys
        35                  40                  45

Thr Phe Gly Asn Val Ser Thr Pro Val Leu Gly Thr Asn Ser Phe Val
    50                  55                  60

Ile Arg Asp Lys Asn Ser Gly Ser Gly Arg Asn Pro Leu Gln Leu Pro
65                  70                  75                  80

Phe Asn Phe Thr Trp Pro Gly Thr Phe Ser Leu Asn Ile Gln Ala Trp
                85                  90                  95

His Thr Pro Gly Asp Asp Leu Arg Pro Glu Thr Ser Pro Gly Asn Ser
            100                 105                 110

Leu Ile Ser Gln Ile Ile Ile Gln Gly Ser Leu Ala Val Gly Lys Asn
        115                 120                 125

Trp Lys Ser Asp Glu Gln Asn Asn Thr Leu Thr Arg Leu Arg Tyr Ser
    130                 135                 140

Tyr Arg Val Val Cys Ser Asp Asn Tyr Tyr Gly Asp Ser Cys Ser Arg
145                 150                 155                 160

Leu Cys Lys Lys Arg Asp Asp His Phe Gly His Tyr Glu Cys Gln Pro
                165                 170                 175

Asp Gly Ser Leu Ser Cys Leu Pro Gly Trp Thr Gly Lys Tyr Cys Asp
            180                 185                 190

Gln Pro Ile Cys Leu Ser Gly Cys His Glu Gln Asn Gly Tyr Cys Ser
        195                 200                 205

Lys Pro Asp Glu Cys Asn Cys Arg Pro Gly Trp Gln Gly Pro Leu Cys
    210                 215                 220

Asn Glu Cys Ile Pro His Asn Gly Cys Arg His Gly Thr Cys Thr Ile
225                 230                 235                 240

Pro Trp Gln Cys Ala Cys Asp Glu Gly Trp Gly Gly Leu Phe Cys Asp
                245                 250                 255

Gln

<210> SEQ ID NO 3
<211> LENGTH: 257
<212> TYPE: PRT
<213> ORGANISM: Rattus norvegicus

<400> SEQUENCE: 3

Ser Ser Ile Phe Gln Leu Arg Leu Gln Glu Phe Ala Asn Glu Arg Gly
1               5                   10                  15

Met Leu Ala Asn Gly Arg Pro Cys Glu Pro Gly Cys Arg Thr Phe Phe
            20                  25                  30

Arg Ile Cys Leu Lys His Tyr Gln Ala Thr Phe Ser Glu Gly Pro Cys
        35                  40                  45

Thr Phe Gly Asn Val Ser Thr Pro Val Leu Gly Thr Asn Ser Phe Val
    50                  55                  60

Ile Arg Asp Lys Asn Ser Gly Ser Gly Arg Asn Pro Leu Gln Leu Pro
65                  70                  75                  80

Leu Asn Phe Thr Trp Pro Gly Thr Phe Ser Leu Ile Ile Gln Ala Trp
```

|  |  |  |  | 85 |  |  |  |  | 90 |  |  |  |  | 95 |  |
|---|---|---|---|---|---|---|---|---|---|---|---|---|---|---|---|

His Thr Pro Gly Asp Asp Leu Arg Pro Glu Thr Ser Pro Gly Asn Ser
                100                 105                 110

Leu Ile Ser Gln Phe Ile Ile Gln Gly Ser Leu Ala Val Gly Lys Asn
            115                 120                 125

Trp Lys Ser Asp Glu Gln Asn Asn Thr Leu Thr Arg Leu Arg Tyr Ser
130                 135                 140

Tyr Arg Val Val Cys Ser Asp Asn Tyr Gly Asp Ser Cys Ser Arg
145                 150                 155                 160

Leu Cys Lys Lys Arg Asp Asp Tyr Phe Gly His Tyr Glu Cys Gln Pro
                165                 170                 175

Asp Gly Ser Pro Ser Cys Leu Pro Gly Trp Thr Gly Glu Tyr Cys Asp
            180                 185                 190

Gln Pro Ile Cys Leu Ser Gly Cys His Glu Gln Asn Gly Tyr Cys Ser
            195                 200                 205

Lys Pro Asp Glu Cys Asn Cys Arg Pro Gly Trp Gln Gly Pro Leu Cys
            210                 215                 220

Asn Glu Cys Ile Pro His Asn Gly Cys Arg His Gly Thr Cys Thr Ile
225                 230                 235                 240

Pro Trp Gln Cys Ala Cys Asp Glu Gly Trp Gly Gly Leu Phe Cys Asp
                245                 250                 255

Gln

<210> SEQ ID NO 4
<211> LENGTH: 1219
<212> TYPE: PRT
<213> ORGANISM: Rattus norvegicus

<400> SEQUENCE: 4

Met Arg Ser Pro Arg Thr Arg Gly Arg Pro Gly Arg Pro Leu Ser Leu
1               5                   10                  15

Leu Leu Ala Leu Leu Cys Ala Leu Arg Ala Lys Val Cys Gly Ala Ser
                20                  25                  30

Gly Gln Phe Glu Leu Glu Ile Leu Ser Met Gln Asn Val Asn Gly Glu
            35                  40                  45

Leu Gln Asn Gly Asn Cys Cys Gly Gly Ala Arg Asn Pro Gly Asp Arg
        50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
                100                 105                 110

Arg Gly Asn Asp Arg Asn Arg Ile Val Leu Pro Phe Ser Phe Ala Trp
            115                 120                 125

Pro Arg Ser Tyr Thr Leu Leu Val Glu Ala Trp Asp Ser Ser Asn Asp
        130                 135                 140

Thr Ile Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Ile
                165                 170                 175

Ala His Phe Glu Tyr Gln Ile Arg Val Thr Cys Asp Asp His Tyr Tyr
            180                 185                 190

Gly Phe Gly Cys Asn Lys Phe Cys Arg Pro Arg Asp Asp Phe Phe Gly

-continued

```
            195                 200                 205
His Tyr Ala Cys Asp Gln Asn Gly Asn Lys Thr Cys Met Glu Gly Trp
210                 215                 220
Met Gly Pro Glu Cys Asn Lys Ala Ile Cys Arg Gln Gly Cys Ser Pro
225                 230                 235                 240
Lys His Gly Ser Cys Lys Leu Pro Gly Asp Cys Arg Cys Gln Tyr Gly
                245                 250                 255
Trp Gln Gly Leu Tyr Cys Asp Lys Cys Ile Pro His Pro Gly Cys Val
                260                 265                 270
His Gly Thr Cys Asn Glu Pro Trp Gln Cys Leu Cys Glu Thr Asn Trp
                275                 280                 285
Gly Gly Gln Leu Cys Asp Lys Asp Leu Asn Tyr Cys Gly Thr His Gln
                290                 295                 300
Pro Cys Leu Asn Arg Gly Thr Cys Ser Asn Thr Gly Pro Asp Lys Tyr
305                 310                 315                 320
Gln Cys Ser Cys Pro Glu Gly Tyr Ser Gly Pro Asn Cys Glu Ile Ala
                325                 330                 335
Glu His Ala Cys Leu Ser Asp Pro Cys His Asn Arg Gly Ser Cys Lys
                340                 345                 350
Glu Thr Ser Ser Gly Phe Glu Cys Glu Cys Ser Pro Gly Trp Thr Gly
                355                 360                 365
Pro Thr Cys Ser Thr Asn Ile Asp Asp Cys Ser Pro Asn Asn Cys Ser
370                 375                 380
His Gly Gly Thr Cys Gln Asp Leu Val Asn Gly Phe Lys Cys Val Cys
385                 390                 395                 400
Pro Pro Gln Trp Thr Gly Lys Thr Cys Gln Leu Asp Ala Asn Glu Cys
                405                 410                 415
Glu Ala Lys Pro Cys Val Asn Ala Arg Ser Cys Lys Asn Leu Ile Ala
                420                 425                 430
Ser Tyr Tyr Cys Asp Cys Leu Pro Gly Trp Met Gly Gln Asn Cys Asp
                435                 440                 445
Ile Asn Ile Asn Asp Cys Leu Gly Gln Cys Gln Asn Asp Ala Ser Cys
                450                 455                 460
Arg Asp Leu Val Asn Gly Tyr Arg Cys Ile Cys Pro Pro Gly Tyr Ala
465                 470                 475                 480
Gly Asp His Cys Glu Arg Asp Ile Asp Glu Cys Ala Ser Asn Pro Cys
                485                 490                 495
Leu Asn Gly Gly His Cys Gln Asn Glu Ile Asn Arg Phe Gln Cys Leu
                500                 505                 510
Cys Pro Thr Gly Phe Ser Gly Asn Leu Cys Gln Leu Asp Ile Asp Tyr
                515                 520                 525
Cys Glu Pro Asn Pro Cys Gln Asn Gly Ala Gln Cys Tyr Asn Arg Ala
                530                 535                 540
Ser Asp Tyr Phe Cys Lys Cys Pro Glu Asp Tyr Glu Gly Lys Asn Cys
545                 550                 555                 560
Ser His Leu Lys Asp His Cys Arg Thr Thr Pro Cys Glu Val Ile Asp
                565                 570                 575
Ser Cys Thr Val Ala Met Ala Ser Asn Asp Thr Pro Glu Gly Val Arg
                580                 585                 590
Tyr Ile Ser Ser Asn Val Cys Gly Pro His Gly Lys Cys Lys Ser Glu
                595                 600                 605
Ser Gly Gly Lys Phe Thr Cys Asp Cys Asn Lys Gly Phe Thr Gly Thr
610                 615                 620
```

```
Tyr Cys His Glu Asn Ile Asn Asp Cys Glu Gly Asn Pro Cys Thr Asn
625                 630                 635                 640

Gly Gly Thr Cys Ile Asp Gly Val Asn Ser Tyr Lys Cys Ile Cys Ser
            645                 650                 655

Asp Gly Trp Glu Gly Ala His Cys Glu Asn Asn Ile Asn Asp Cys Ser
                660                 665                 670

Gln Asn Pro Cys His Tyr Gly Gly Thr Cys Arg Asp Leu Val Asn Asp
            675                 680                 685

Phe Tyr Cys Asp Cys Lys Asn Gly Trp Lys Gly Lys Thr Cys His Ser
690                 695                 700

Arg Asp Ser Gln Cys Asp Glu Ala Thr Cys Asn Asn Gly Gly Thr Cys
705                 710                 715                 720

Tyr Asp Glu Val Asp Thr Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Asp Ser Phe Thr Cys
            755                 760                 765

Val Cys Lys Glu Gly Trp Glu Gly Pro Ile Cys Thr Gln Asn Thr Asn
770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Gln Cys Ile Cys Pro Pro
            835                 840                 845

Gly His Ser Gly Ala Lys Cys His Glu Val Ser Gly Arg Ser Cys Ile
850                 855                 860

Thr Met Gly Arg Val Ile Leu Asp Gly Ala Lys Trp Asp Asp Asp Cys
865                 870                 875                 880

Asn Thr Cys Gln Cys Leu Asn Gly Arg Val Ala Cys Ser Lys Val Trp
            885                 890                 895

Cys Gly Pro Arg Pro Cys Gln Leu His Lys Gly His Gly Glu Cys Pro
            900                 905                 910

Asn Gly Gln Ser Cys Ile Pro Val Leu Asp Asp Gln Cys Phe Val Arg
            915                 920                 925

Pro Cys Thr Gly Ala Gly Glu Cys Arg Ser Ser Leu Gln Pro Val
            930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile Ala Cys Glu Pro Ser Leu Ser Ala
            995                 1000                1005

Asn Asn Glu Ile His Val Ala Ile Ser Ala Glu Asp Ile Arg Asp
        1010                1015                1020

Asp Gly Asn Pro Val Lys Glu Ile Thr Asp Lys Ile Ile Asp Leu
        1025                1030                1035
```

```
Val Ser Lys Arg Asp Gly Asn Ser Ser Leu Ile Ala Ala Val Ala
    1040                1045                1050

Glu Val Arg Val Gln Arg Arg Pro Leu Lys Asn Arg Thr Asp Phe
    1055                1060                1065

Leu Val Pro Leu Leu Ser Ser Val Leu Thr Val Ala Trp Val Cys
    1070                1075                1080

Cys Leu Val Thr Ala Phe Tyr Trp Cys Val Arg Lys Arg Arg Arg
    1085                1090                1095

Lys Pro Ser Ser His Thr His Ser Ala Pro Glu Asp Asn Thr Thr
    1100                1105                1110

Asn Asn Val Arg Glu Gln Leu Asn Gln Ile Lys Asn Pro Ile Glu
    1115                1120                1125

Lys His Gly Ala Asn Thr Val Pro Ile Lys Asp Tyr Glu Asn Lys
    1130                1135                1140

Asn Ser Lys Met Ser Lys Ile Arg Thr His Asn Ser Glu Val Glu
    1145                1150                1155

Glu Asp Asp Met Asp Lys His Gln Gln Lys Val Arg Phe Ala Lys
    1160                1165                1170

Gln Pro Val Tyr Thr Leu Val Asp Arg Glu Glu Lys Ala Pro Ser
    1175                1180                1185

Gly Thr Pro Thr Lys His Pro Asn Trp Thr Asn Lys Gln Asp Asn
    1190                1195                1200

Arg Asp Leu Glu Ser Ala Gln Ser Leu Asn Arg Met Glu Tyr Ile
    1205                1210                1215

Val

<210> SEQ ID NO 5
<211> LENGTH: 264
<212> TYPE: PRT
<213> ORGANISM: Rattus norvegicus

<400> SEQUENCE: 5

Ser Gly Gln Phe Glu Leu Glu Ile Leu Ser Met Gln Asn Val Asn Gly
1               5                   10                  15

Glu Leu Gln Asn Gly Asn Cys Cys Gly Gly Ala Arg Asn Pro Gly Asp
                20                  25                  30

Arg Lys Cys Thr Arg Asp Glu Cys Asp Thr Tyr Phe Lys Val Cys Leu
            35                  40                  45

Lys Glu Tyr Gln Ser Arg Val Thr Ala Gly Gly Pro Cys Ser Phe Gly
    50                  55                  60

Ser Gly Ser Thr Pro Val Ile Gly Gly Asn Thr Phe Asn Leu Lys Ala
65                  70                  75                  80

Ser Arg Gly Asn Asp Arg Asn Arg Ile Val Leu Pro Phe Ser Phe Ala
                85                  90                  95

Trp Pro Arg Ser Tyr Thr Leu Leu Val Glu Ala Trp Asp Ser Ser Asn
                100                 105                 110

Asp Thr Ile Gln Pro Asp Ser Ile Glu Lys Ala Ser His Ser Gly
            115                 120                 125

Met Ile Asn Pro Ser Arg Gln Trp Gln Thr Leu Lys Gln Asn Thr Gly
    130                 135                 140

Ile Ala His Phe Glu Tyr Gln Ile Arg Val Thr Cys Asp Asp His Tyr
145                 150                 155                 160

Tyr Gly Phe Gly Cys Asn Lys Phe Cys Arg Pro Arg Asp Asp Phe Phe
                165                 170                 175
```

```
Gly His Tyr Ala Cys Asp Gln Asn Gly Asn Lys Thr Cys Met Glu Gly
                180                 185                 190

Trp Met Gly Pro Glu Cys Asn Lys Ala Ile Cys Arg Gln Gly Cys Ser
            195                 200                 205

Pro Lys His Gly Ser Cys Lys Leu Pro Gly Asp Cys Arg Cys Gln Tyr
        210                 215                 220

Gly Trp Gln Gly Leu Tyr Cys Asp Lys Cys Ile Pro His Pro Gly Cys
225                 230                 235                 240

Val His Gly Thr Cys Asn Glu Pro Trp Gln Cys Leu Cys Glu Thr Asn
                245                 250                 255

Trp Gly Gly Gln Leu Cys Asp Lys
            260

<210> SEQ ID NO 6
<211> LENGTH: 317
<212> TYPE: PRT
<213> ORGANISM: Homo sapiens

<400> SEQUENCE: 6

Tyr Phe Glu Leu Gln Leu Ser Ala Leu Arg Asn Val Asn Gly Glu Leu
1               5                   10                  15

Leu Ser Gly Ala Cys Cys Asp Gly Asp Gly Arg Thr Thr Arg Ala Gly
            20                  25                  30

Gly Cys Gly His Asp Glu Cys Asp Thr Tyr Val Arg Val Cys Leu Lys
        35                  40                  45

Glu Tyr Gln Ala Lys Val Thr Pro Thr Gly Pro Cys Ser Tyr Gly His
    50                  55                  60

Gly Ala Thr Pro Val Leu Gly Gly Asn Ser Phe Tyr Leu Pro Pro Ala
65                  70                  75                  80

Gly Ala Ala Gly Asp Arg Ala Arg Ala Arg Ala Arg Ala Gly Gly Asp
                85                  90                  95

Gln Asp Pro Gly Leu Val Val Ile Pro Phe Gln Phe Ala Trp Pro Arg
            100                 105                 110

Ser Phe Thr Leu Ile Val Glu Ala Trp Asp Trp Asp Asn Asp Thr Thr
        115                 120                 125

Pro Asn Glu Glu Leu Leu Ile Glu Arg Val Ser His Ala Gly Met Ile
130                 135                 140

Asn Pro Glu Asp Arg Trp Lys Ser Leu His Phe Ser Gly His Val Ala
145                 150                 155                 160

His Leu Glu Leu Gln Ile Arg Val Arg Cys Asp Glu Asn Tyr Tyr Ser
                165                 170                 175

Ala Thr Cys Asn Lys Phe Cys Arg Pro Arg Asn Asp Phe Phe Gly His
            180                 185                 190

Tyr Thr Cys Asp Gln Tyr Gly Asn Lys Ala Cys Met Asp Gly Trp Met
        195                 200                 205

Gly Lys Glu Cys Lys Glu Ala Val Cys Lys Gln Gly Cys Asn Leu Leu
    210                 215                 220

His Gly Gly Cys Thr Val Pro Gly Glu Cys Arg Cys Ser Tyr Gly Trp
225                 230                 235                 240

Gln Gly Arg Phe Cys Asp Glu Cys Val Pro Tyr Pro Gly Cys Val His
                245                 250                 255

Gly Ser Cys Val Glu Pro Trp Gln Cys Asn Cys Glu Thr Asn Trp Gly
            260                 265                 270

Gly Leu Leu Cys Asp Lys Asp Leu Asn Tyr Cys Gly Ser His His Pro
        275                 280                 285
```

Cys Thr Asn Gly Gly Thr Cys Ile Asn Ala Glu Pro Asp Gln Tyr Arg
            290                 295                 300

Cys Thr Cys Pro Asp Gly Tyr Ser Gly Arg Asn Cys Glu
305                 310                 315

<210> SEQ ID NO 7
<211> LENGTH: 305
<212> TYPE: PRT
<213> ORGANISM: Homo sapiens

<400> SEQUENCE: 7

Ser Gly Val Phe Glu Leu Lys Leu Gln Glu Phe Val Asn Lys Lys Gly
1               5                   10                  15

Leu Leu Gly Asn Arg Asn Cys Cys Arg Gly Ala Gly Pro Pro Pro
            20                  25                  30

Cys Ala Cys Arg Thr Phe Phe Arg Val Cys Leu Lys His Tyr Gln Ala
        35                  40                  45

Ser Val Ser Pro Glu Pro Pro Cys Thr Tyr Gly Ser Ala Val Thr Pro
    50                  55                  60

Val Leu Gly Val Asp Ser Phe Ser Leu Pro Asp Gly Gly Gly Ala Asp
65                  70                  75                  80

Ser Ala Phe Ser Asn Pro Ile Arg Phe Pro Phe Gly Phe Thr Trp Pro
                85                  90                  95

Gly Thr Phe Ser Leu Ile Ile Glu Ala Leu His Thr Asp Ser Pro Asp
            100                 105                 110

Asp Leu Ala Thr Glu Asn Pro Glu Arg Leu Ile Ser Arg Leu Ala Thr
        115                 120                 125

Gln Arg His Leu Thr Val Gly Glu Glu Trp Ser Gln Asp Leu His Ser
    130                 135                 140

Ser Gly Arg Thr Asp Leu Lys Tyr Ser Tyr Arg Phe Val Cys Asp Glu
145                 150                 155                 160

His Tyr Tyr Gly Glu Gly Cys Ser Val Phe Cys Arg Pro Arg Asp Asp
                165                 170                 175

Ala Phe Gly His Phe Thr Cys Gly Glu Arg Gly Glu Lys Val Cys Asn
            180                 185                 190

Pro Gly Trp Lys Gly Pro Tyr Cys Thr Glu Pro Ile Cys Leu Pro Gly
        195                 200                 205

Cys Asp Glu Gln His Gly Phe Cys Asp Lys Pro Gly Glu Cys Lys Cys
    210                 215                 220

Arg Val Gly Trp Gln Gly Arg Tyr Cys Asp Glu Cys Ile Arg Tyr Pro
225                 230                 235                 240

Gly Cys Leu His Gly Thr Cys Gln Gln Pro Trp Gln Cys Asn Cys Gln
                245                 250                 255

Glu Gly Trp Gly Gly Leu Phe Cys Asn Gln Asp Leu Asn Tyr Cys Thr
            260                 265                 270

His His Lys Pro Cys Lys Asn Gly Ala Thr Cys Thr Asn Thr Gly Gln
        275                 280                 285

Gly Ser Tyr Thr Cys Ser Cys Arg Pro Gly Tyr Thr Gly Ala Thr Cys
    290                 295                 300

Glu
305

<210> SEQ ID NO 8
<211> LENGTH: 2555
<212> TYPE: PRT

<213> ORGANISM: Homo sapiens

<400> SEQUENCE: 8

```
Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
            180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
    210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
        275                 280                 285

Gly Gln Tyr Cys Thr Glu Asp Val Asp Glu Cys Gln Leu Met Pro Asn
    290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
        355                 360                 365

Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400
```

```
Pro Ser Gly Tyr Thr Gly Pro Ala Cys Ser Gln Asp Val Asp Glu Cys
            405                 410                 415

Ser Leu Gly Ala Asn Pro Cys Glu His Ala Gly Lys Cys Ile Asn Thr
        420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Val Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
        500                 505                 510

Gln Cys Glu Cys Pro Thr Gly Phe Thr Gly His Leu Cys Gln Tyr Asp
    515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
        580                 585                 590

Pro Gly Tyr Thr Gly His His Cys Glu Thr Asn Ile Asn Glu Cys Ser
        595                 600                 605

Ser Gln Pro Cys Arg His Gly Gly Thr Cys Gln Asp Arg Asp Asn Ala
    610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
        660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
        690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
        740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
```

```
                    820             825                  830
Cys Ala Pro Ser Pro Cys Arg Asn Gly Gly Glu Cys Arg Gln Ser Glu
            835                 840                 845

Asp Tyr Glu Ser Phe Ser Cys Val Cys Pro Thr Gly Trp Gln Gly Gln
        850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
            900                 905                 910

Pro Asn Pro Cys His Asn Gly Gly Ser Cys Thr Asp Gly Ile Asn Thr
        915                 920                 925

Ala Phe Cys Asp Cys Leu Pro Gly Phe Arg Gly Thr Phe Cys Glu Glu
    930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
                965                 970                 975

Gly Ile His Cys Glu Asn Asn Thr Pro Asp Cys Thr Glu Ser Ser Cys
            980                 985                 990

Phe Asn Gly Gly Thr Cys Val Asp Gly Ile Asn Ser Phe Thr Cys Leu
        995                 1000                1005

Cys Pro Pro Gly Phe Thr Gly Ser Tyr Cys Gln His Asp Val Asn
    1010                1015                1020

Glu Cys Asp Ser Gln Pro Cys Leu His Gly Gly Thr Cys Gln Asp
    1025                1030                1035

Gly Cys Gly Ser Tyr Arg Cys Thr Cys Pro Gln Gly Tyr Thr Gly
    1040                1045                1050

Pro Asn Cys Gln Asn Leu Val His Trp Cys Asp Ser Ser Pro Cys
    1055                1060                1065

Lys Asn Gly Gly Lys Cys Trp Gln Thr His Thr Gln Tyr Arg Cys
    1070                1075                1080

Glu Cys Pro Ser Gly Trp Thr Gly Leu Tyr Cys Asp Val Pro Ser
    1085                1090                1095

Val Ser Cys Glu Val Ala Ala Gln Arg Gln Gly Val Asp Val Ala
    1100                1105                1110

Arg Leu Cys Gln His Gly Gly Leu Cys Val Asp Ala Gly Asn Thr
    1115                1120                1125

His His Cys Arg Cys Gln Ala Gly Tyr Thr Gly Ser Tyr Cys Glu
    1130                1135                1140

Asp Leu Val Asp Glu Cys Ser Pro Ser Pro Cys Gln Asn Gly Ala
    1145                1150                1155

Thr Cys Thr Asp Tyr Leu Gly Gly Tyr Ser Cys Lys Cys Val Ala
    1160                1165                1170

Gly Tyr His Gly Val Asn Cys Ser Glu Glu Ile Asp Glu Cys Leu
    1175                1180                1185

Ser His Pro Cys Gln Asn Gly Gly Thr Cys Leu Asp Leu Pro Asn
    1190                1195                1200

Thr Tyr Lys Cys Ser Cys Pro Arg Gly Thr Gln Gly Val His Cys
    1205                1210                1215

Glu Ile Asn Val Asp Asp Cys Asn Pro Pro Val Asp Pro Val Ser
    1220                1225                1230
```

```
Arg Ser Pro Lys Cys Phe Asn Asn Gly Thr Cys Val Asp Gln Val
    1235            1240            1245

Gly Gly Tyr Ser Cys Thr Cys Pro Pro Gly Phe Val Gly Glu Arg
    1250            1255            1260

Cys Glu Gly Asp Val Asn Glu Cys Leu Ser Asn Pro Cys Asp Ala
    1265            1270            1275

Arg Gly Thr Gln Asn Cys Val Gln Arg Val Asn Asp Phe His Cys
    1280            1285            1290

Glu Cys Arg Ala Gly His Thr Gly Arg Arg Cys Glu Ser Val Ile
    1295            1300            1305

Asn Gly Cys Lys Gly Lys Pro Cys Lys Asn Gly Gly Thr Cys Ala
    1310            1315            1320

Val Ala Ser Asn Thr Ala Arg Gly Phe Ile Cys Lys Cys Pro Ala
    1325            1330            1335

Gly Phe Glu Gly Ala Thr Cys Glu Asn Asp Ala Arg Thr Cys Gly
    1340            1345            1350

Ser Leu Arg Cys Leu Asn Gly Gly Thr Cys Ile Ser Gly Pro Arg
    1355            1360            1365

Ser Pro Thr Cys Leu Cys Leu Gly Pro Phe Thr Gly Pro Glu Cys
    1370            1375            1380

Gln Phe Pro Ala Ser Ser Pro Cys Leu Gly Gly Asn Pro Cys Tyr
    1385            1390            1395

Asn Gln Gly Thr Cys Glu Pro Thr Ser Glu Ser Pro Phe Tyr Arg
    1400            1405            1410

Cys Leu Cys Pro Ala Lys Phe Asn Gly Leu Leu Cys His Ile Leu
    1415            1420            1425

Asp Tyr Ser Phe Gly Gly Gly Ala Gly Arg Asp Ile Pro Pro Pro
    1430            1435            1440

Leu Ile Glu Glu Ala Cys Glu Leu Pro Glu Cys Gln Glu Asp Ala
    1445            1450            1455

Gly Asn Lys Val Cys Ser Leu Gln Cys Asn Asn His Ala Cys Gly
    1460            1465            1470

Trp Asp Gly Gly Asp Cys Ser Leu Asn Phe Asn Asp Pro Trp Lys
    1475            1480            1485

Asn Cys Thr Gln Ser Leu Gln Cys Trp Lys Tyr Phe Ser Asp Gly
    1490            1495            1500

His Cys Asp Ser Gln Cys Asn Ser Ala Gly Cys Leu Phe Asp Gly
    1505            1510            1515

Phe Asp Cys Gln Arg Ala Glu Gly Gln Cys Asn Pro Leu Tyr Asp
    1520            1525            1530

Gln Tyr Cys Lys Asp His Phe Ser Asp Gly His Cys Asp Gln Gly
    1535            1540            1545

Cys Asn Ser Ala Glu Cys Glu Trp Asp Gly Leu Asp Cys Ala Glu
    1550            1555            1560

His Val Pro Glu Arg Leu Ala Ala Gly Thr Leu Val Val Val Val
    1565            1570            1575

Leu Met Pro Pro Glu Gln Leu Arg Asn Ser Ser Phe His Phe Leu
    1580            1585            1590

Arg Glu Leu Ser Arg Val Leu His Thr Asn Val Val Phe Lys Arg
    1595            1600            1605

Asp Ala His Gly Gln Gln Met Ile Phe Pro Tyr Tyr Gly Arg Glu
    1610            1615            1620
```

```
Glu Glu Leu Arg Lys His Pro Ile Lys Arg Ala Ala Glu Gly Trp
    1625                1630                1635

Ala Ala Pro Asp Ala Leu Leu Gly Gln Val Lys Ala Ser Leu Leu
    1640                1645                1650

Pro Gly Gly Ser Glu Gly Gly Arg Arg Arg Glu Leu Asp Pro
    1655                1660                1665

Met Asp Val Arg Gly Ser Ile Val Tyr Leu Glu Ile Asp Asn Arg
    1670                1675                1680

Gln Cys Val Gln Ala Ser Ser Gln Cys Phe Gln Ser Ala Thr Asp
    1685                1690                1695

Val Ala Ala Phe Leu Gly Ala Leu Ala Ser Leu Gly Ser Leu Asn
    1700                1705                1710

Ile Pro Tyr Lys Ile Glu Ala Val Gln Ser Glu Thr Val Glu Pro
    1715                1720                1725

Pro Pro Pro Ala Gln Leu His Phe Met Tyr Val Ala Ala Ala Ala
    1730                1735                1740

Phe Val Leu Leu Phe Phe Val Gly Cys Gly Val Leu Leu Ser Arg
    1745                1750                1755

Lys Arg Arg Arg Gln His Gly Gln Leu Trp Phe Pro Glu Gly Phe
    1760                1765                1770

Lys Val Ser Glu Ala Ser Lys Lys Lys Arg Arg Glu Pro Leu Gly
    1775                1780                1785

Glu Asp Ser Val Gly Leu Lys Pro Leu Lys Asn Ala Ser Asp Gly
    1790                1795                1800

Ala Leu Met Asp Asp Asn Gln Asn Glu Trp Gly Asp Glu Asp Leu
    1805                1810                1815

Glu Thr Lys Lys Phe Arg Phe Glu Glu Pro Val Val Leu Pro Asp
    1820                1825                1830

Leu Asp Asp Gln Thr Asp His Arg Gln Trp Thr Gln Gln His Leu
    1835                1840                1845

Asp Ala Ala Asp Leu Arg Met Ser Ala Met Ala Pro Thr Pro Pro
    1850                1855                1860

Gln Gly Glu Val Asp Ala Asp Cys Met Asp Val Asn Val Arg Gly
    1865                1870                1875

Pro Asp Gly Phe Thr Pro Leu Met Ile Ala Ser Cys Ser Gly Gly
    1880                1885                1890

Gly Leu Glu Thr Gly Asn Ser Glu Glu Glu Glu Asp Ala Pro Ala
    1895                1900                1905

Val Ile Ser Asp Phe Ile Tyr Gln Gly Ala Ser Leu His Asn Gln
    1910                1915                1920

Thr Asp Arg Thr Gly Glu Thr Ala Leu His Leu Ala Ala Arg Tyr
    1925                1930                1935

Ser Arg Ser Asp Ala Ala Lys Arg Leu Leu Glu Ala Ser Ala Asp
    1940                1945                1950

Ala Asn Ile Gln Asp Asn Met Gly Arg Thr Pro Leu His Ala Ala
    1955                1960                1965

Val Ser Ala Asp Ala Gln Gly Val Phe Gln Ile Leu Ile Arg Asn
    1970                1975                1980

Arg Ala Thr Asp Leu Asp Ala Arg Met His Asp Gly Thr Thr Pro
    1985                1990                1995

Leu Ile Leu Ala Ala Arg Leu Ala Val Glu Gly Met Leu Glu Asp
    2000                2005                2010

Leu Ile Asn Ser His Ala Asp Val Asn Ala Val Asp Asp Leu Gly
```

```
                    2015                    2020                    2025
Lys Ser Ala Leu His Trp Ala Ala Val Asn Asn Val Asp Ala
        2030            2035                2040

Ala Val Val Leu Leu Lys Asn Gly Ala Asn Lys Asp Met Gln Asn
        2045            2050                2055

Asn Arg Glu Glu Thr Pro Leu Phe Leu Ala Ala Arg Glu Gly Ser
        2060            2065                2070

Tyr Glu Thr Ala Lys Val Leu Leu Asp His Phe Ala Asn Arg Asp
        2075            2080                2085

Ile Thr Asp His Met Asp Arg Leu Pro Arg Asp Ile Ala Gln Glu
        2090            2095                2100

Arg Met His His Asp Ile Val Arg Leu Leu Asp Glu Tyr Asn Leu
        2105            2110                2115

Val Arg Ser Pro Gln Leu His Gly Ala Pro Leu Gly Gly Thr Pro
        2120            2125                2130

Thr Leu Ser Pro Pro Leu Cys Ser Pro Asn Gly Tyr Leu Gly Ser
        2135            2140                2145

Leu Lys Pro Gly Val Gln Gly Lys Lys Val Arg Lys Pro Ser Ser
        2150            2155                2160

Lys Gly Leu Ala Cys Gly Ser Lys Glu Ala Lys Asp Leu Lys Ala
        2165            2170                2175

Arg Arg Lys Lys Ser Gln Asp Gly Lys Gly Cys Leu Leu Asp Ser
        2180            2185                2190

Ser Gly Met Leu Ser Pro Val Asp Ser Leu Glu Ser Pro His Gly
        2195            2200                2205

Tyr Leu Ser Asp Val Ala Ser Pro Pro Leu Leu Pro Ser Pro Phe
        2210            2215                2220

Gln Gln Ser Pro Ser Val Pro Leu Asn His Leu Pro Gly Met Pro
        2225            2230                2235

Asp Thr His Leu Gly Ile Gly His Leu Asn Val Ala Ala Lys Pro
        2240            2245                2250

Glu Met Ala Ala Leu Gly Gly Gly Gly Arg Leu Ala Phe Glu Thr
        2255            2260                2265

Gly Pro Pro Arg Leu Ser His Leu Pro Val Ala Ser Gly Thr Ser
        2270            2275                2280

Thr Val Leu Gly Ser Ser Ser Gly Gly Ala Leu Asn Phe Thr Val
        2285            2290                2295

Gly Gly Ser Thr Ser Leu Asn Gly Gln Cys Glu Trp Leu Ser Arg
        2300            2305                2310

Leu Gln Ser Gly Met Val Pro Asn Gln Tyr Asn Pro Leu Arg Gly
        2315            2320                2325

Ser Val Ala Pro Gly Pro Leu Ser Thr Gln Ala Pro Ser Leu Gln
        2330            2335                2340

His Gly Met Val Gly Pro Leu His Ser Ser Leu Ala Ala Ser Ala
        2345            2350                2355

Leu Ser Gln Met Met Ser Tyr Gln Gly Leu Pro Ser Thr Arg Leu
        2360            2365                2370

Ala Thr Gln Pro His Leu Val Gln Thr Gln Gln Val Gln Pro Gln
        2375            2380                2385

Asn Leu Gln Met Gln Gln Gln Asn Leu Gln Pro Ala Asn Ile Gln
        2390            2395                2400

Gln Gln Gln Ser Leu Gln Pro Pro Pro Pro Pro Gln Pro His
        2405            2410                2415
```

```
Leu Gly Val Ser Ser Ala Ala Ser Gly His Leu Gly Arg Ser Phe
    2420            2425                2430

Leu Ser Gly Glu Pro Ser Gln Ala Asp Val Gln Pro Leu Gly Pro
    2435            2440                2445

Ser Ser Leu Ala Val His Thr Ile Leu Pro Gln Glu Ser Pro Ala
    2450            2455                2460

Leu Pro Thr Ser Leu Pro Ser Ser Leu Val Pro Val Thr Ala
    2465            2470                2475

Ala Gln Phe Leu Thr Pro Pro Ser Gln His Ser Tyr Ser Ser Pro
    2480            2485                2490

Val Asp Asn Thr Pro Ser His Gln Leu Gln Val Pro Glu His Pro
    2495            2500                2505

Phe Leu Thr Pro Ser Pro Glu Ser Pro Asp Gln Trp Ser Ser Ser
    2510            2515                2520

Ser Pro His Ser Asn Val Ser Asp Trp Ser Glu Gly Val Ser Ser
    2525            2530                2535

Pro Pro Thr Ser Met Gln Ser Gln Ile Ala Arg Ile Pro Glu Ala
    2540            2545                2550

Phe Lys
    2555

<210> SEQ ID NO 9
<211> LENGTH: 243
<212> TYPE: PRT
<213> ORGANISM: Artificial Sequence
<220> FEATURE:
<223> OTHER INFORMATION: Anti-CD33 single-chain variable fragment

<400> SEQUENCE: 9

Ser Glu Val Gln Leu Gln Gln Ser Gly Pro Glu Val Val Lys Pro Gly
1               5                   10                  15

Ala Ser Val Lys Met Ser Cys Lys Ala Ser Gly Tyr Thr Ile Thr Asp
            20                  25                  30

Ser Asn Ile His Trp Val Lys Gln Ser Arg Gly Lys Ser Leu Glu Trp
        35                  40                  45

Ile Gly Tyr Ile Tyr Pro Tyr Asn Gly Gly Thr Asp Tyr Asn Gln Lys
    50                  55                  60

Phe Lys Asn Lys Ala Thr Leu Thr Val Asp Asn Pro Ser Ser Thr Ala
65                  70                  75                  80

Tyr Met Glu Leu Arg Ser Leu Thr Ser Glu Asp Ser Ala Val Tyr Tyr
                85                  90                  95

Cys Val Asn Gly Asn Pro Trp Leu Ala Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Gly Ser Asp Ile Val Leu Thr Gln Ser Pro Ala Ser Leu Ala
    130                 135                 140

Val Ser Leu Gly Gln Arg Ala Thr Ile Ser Cys Arg Ala Ser Glu Ser
145                 150                 155                 160

Leu Asp Asn Tyr Gly Ile Arg Phe Leu Thr Trp Phe Gln Gln Arg Pro
                165                 170                 175

Gly Gln Pro Pro Lys Leu Leu Ile Tyr Ala Ala Ser Asn Gln Gly Ser
            180                 185                 190

Gly Val Pro Ala Arg Phe Ser Gly Ser Gly Ser Gly Thr Glu Phe Ser
        195                 200                 205
```

```
Leu Asn Ile His Pro Met Glu Glu Asp Asp Thr Ala Ile Tyr Phe Cys
    210                 215                 220

Gln Gln Thr Lys Glu Val Pro Trp Ser Phe Gly Gly Gly Thr Lys Leu
225                 230                 235                 240

Glu Ile Lys

<210> SEQ ID NO 10
<211> LENGTH: 765
<212> TYPE: PRT
<213> ORGANISM: Artificial Sequence
<220> FEATURE:
<223> OTHER INFORMATION: ANti-CD33 single-chain variable fragment

<400> SEQUENCE: 10

Ser Ser Ile Phe Gln Leu Arg Leu Gln Glu Phe Ala Asn Glu Arg Gly
1               5                   10                  15

Met Leu Ala Asn Gly Arg Pro Cys Glu Pro Gly Cys Arg Thr Phe Phe
            20                  25                  30

Arg Ile Cys Leu Lys His Tyr Gln Ala Thr Phe Ser Glu Gly Pro Cys
        35                  40                  45

Thr Phe Gly Asn Val Ser Thr Pro Val Leu Gly Thr Asn Ser Phe Val
    50                  55                  60

Ile Arg Asp Lys Asn Ser Gly Ser Gly Arg Asn Pro Leu Gln Leu Pro
65                  70                  75                  80

Leu Asn Phe Thr Trp Pro Gly Thr Phe Ser Leu Ile Ile Gln Ala Trp
                85                  90                  95

His Thr Pro Gly Asp Asp Leu Arg Pro Glu Thr Ser Pro Gly Asn Ser
            100                 105                 110

Leu Ile Ser Gln Phe Ile Ile Gln Gly Ser Leu Ala Val Gly Lys Asn
        115                 120                 125

Trp Lys Ser Asp Glu Gln Asn Asn Thr Leu Thr Arg Leu Arg Tyr Ser
    130                 135                 140

Tyr Arg Val Val Cys Ser Asp Asn Tyr Tyr Gly Asp Ser Cys Ser Arg
145                 150                 155                 160

Leu Cys Lys Lys Arg Asp Asp Tyr Phe Gly His Tyr Glu Cys Gln Pro
                165                 170                 175

Asp Gly Ser Pro Ser Cys Leu Pro Gly Trp Thr Gly Glu Tyr Cys Asp
            180                 185                 190

Gln Pro Ile Cys Leu Ser Gly Cys His Glu Gln Asn Gly Tyr Cys Ser
        195                 200                 205

Lys Pro Asp Glu Cys Asn Cys Arg Pro Gly Trp Gln Gly Pro Leu Cys
    210                 215                 220

Asn Glu Cys Ile Pro His Asn Gly Cys Arg His Gly Thr Cys Thr Ile
225                 230                 235                 240

Pro Trp Gln Cys Ala Cys Asp Glu Gly Trp Gly Gly Leu Phe Cys Asp
                245                 250                 255

Gln Asp Leu Asn Tyr Cys Thr His His Ser Pro Cys Lys Asn Gly Ser
            260                 265                 270

Thr Cys Ser Asn Ser Gly Pro Arg Gly Tyr Thr Cys Thr Cys Leu Pro
        275                 280                 285

Gly Tyr Thr Gly Glu His Cys Glu Leu Glu Leu Ser Lys Cys Ala Ser
    290                 295                 300

Asn Pro Cys Arg Asn Gly Gly Ser Cys Lys Asp His Glu Asn Ser Tyr
305                 310                 315                 320
```

```
His Cys Leu Cys Pro Pro Gly Tyr Tyr Gly Gln His Cys Glu His Ser
                325                 330                 335

Thr Leu Thr Cys Ala Asp Ser Pro Cys Phe Asn Gly Gly Ser Cys Arg
            340                 345                 350

Glu Arg Asn Gln Gly Ala Ser Tyr Ala Cys Glu Cys Pro Pro Asn Phe
        355                 360                 365

Thr Gly Ser Asn Cys Glu Lys Lys Val Asp Arg Cys Thr Ser Asn Pro
    370                 375                 380

Cys Ala Asn Gly Gly Gln Cys Leu Asn Arg Gly Pro Ser Arg Thr Cys
385                 390                 395                 400

Arg Cys Arg Pro Gly Phe Thr Gly Thr His Cys Glu Leu His Ile Ser
                405                 410                 415

Asp Cys Ala Arg Ser Pro Cys Ala His Gly Thr Cys His Asp Leu
            420                 425                 430

Glu Asn Gly Pro Val Cys Thr Cys Pro Ala Gly Phe Ser Gly Arg Arg
        435                 440                 445

Cys Glu Val Arg Ile Thr Asn Asp Ala Cys Ala Ser Gly Pro Cys Phe
450                 455                 460

Asn Gly Ala Thr Cys Tyr Thr Gly Leu Ser Pro Asn Asn Phe Val Cys
465                 470                 475                 480

Asn Cys Pro Tyr Gly Phe Val Gly Ser Arg Cys Glu Gly Ser Gly Ser
                485                 490                 495

Gly Ser Gly Ser Gly Ser Glu Val Gln Leu Gln Gln Ser Gly Pro Glu
                500                 505                 510

Val Val Lys Pro Gly Ala Ser Val Lys Met Ser Cys Lys Ala Ser Gly
            515                 520                 525

Tyr Thr Ile Thr Asp Ser Asn Ile His Trp Val Lys Gln Ser Arg Gly
        530                 535                 540

Lys Ser Leu Glu Trp Ile Gly Tyr Ile Tyr Pro Tyr Asn Gly Gly Thr
545                 550                 555                 560

Asp Tyr Asn Gln Lys Phe Lys Asn Lys Ala Thr Leu Thr Val Asp Asn
                565                 570                 575

Pro Ser Ser Thr Ala Tyr Met Glu Leu Arg Ser Leu Thr Ser Glu Asp
            580                 585                 590

Ser Ala Val Tyr Tyr Cys Val Asn Gly Asn Pro Trp Leu Ala Tyr Trp
        595                 600                 605

Gly Gln Gly Thr Leu Val Thr Val Ser Ala Gly Gly Gly Gly Ser Gly
    610                 615                 620

Gly Gly Gly Ser Gly Gly Gly Gly Ser Asp Ile Val Leu Thr Gln Ser
625                 630                 635                 640

Pro Ala Ser Leu Ala Val Ser Leu Gly Gln Arg Ala Thr Ile Ser Cys
                645                 650                 655

Arg Ala Ser Glu Ser Leu Asp Asn Tyr Gly Ile Arg Phe Leu Thr Trp
            660                 665                 670

Phe Gln Gln Arg Pro Gly Gln Pro Pro Lys Leu Leu Ile Tyr Ala Ala
        675                 680                 685

Ser Asn Gln Gly Ser Gly Val Pro Ala Arg Phe Ser Gly Ser Gly Ser
    690                 695                 700

Gly Thr Glu Phe Ser Leu Asn Ile His Pro Met Glu Glu Asp Asp Thr
705                 710                 715                 720
```

```
Ala Ile Tyr Phe Cys Gln Gln Thr Lys Glu Val Pro Trp Ser Phe Gly
            725                 730                 735

Gly Gly Thr Lys Leu Glu Ile Lys Glu Gln Lys Leu Ile Ser Glu Glu
            740                 745                 750

Asp Leu Ala Ala Ala His His His His His His His
            755                 760             765
```